United States Patent [19]
Taketani et al.

[11] Patent Number: 5,998,674
[45] Date of Patent: Dec. 7, 1999

[54] BROMINE COMPOUND PRODUCTION METHOD

[75] Inventors: Yutaka Taketani; Haruhisa Hoshimi; Masanori Monri; Seiichi Tanabe; Yasuhiro Shimidzu, all of Chiyoda-ku, Japan

[73] Assignee: Teijin Chemicals, Ltd., Tokyo, Japan

[21] Appl. No.: 09/137,534

[22] Filed: Aug. 21, 1998

[51] Int. Cl.$^6$ .................................................. C07C 43/02
[52] U.S. Cl. ........................ 568/634; 568/655; 568/641; 568/669; 568/31; 568/42; 568/55; 568/361; 568/308; 257/608; 257/609
[58] Field of Search ..................... 568/634, 630, 568/649, 655, 669, 33, 31, 42, 55, 367, 308, 641; 252/608, 609

[56] References Cited

U.S. PATENT DOCUMENTS 3,895,077  7/1975  Brady .
4,006,118  2/1977  Ogawa .

FOREIGN PATENT DOCUMENTS 49-39655   10/1974  Japan .
50-30853   3/1975   Japan .
50-23693   8/1975   Japan .
55-111429  8/1980   Japan .
03271267   12/1991  Japan .
04234354   8/1992   Japan .
07173092   7/1995   Japan .
07316087   12/1995  Japan .

OTHER PUBLICATIONS

WPIDS acc No. 93–216749 abs of JP05140083, Nov. 1991.

Primary Examiner—Gary Geist
Assistant Examiner—Jean F Vallano
Attorney, Agent, or Firm—Sherman and Shalloway

[57] ABSTRACT

Method of producing a bromine compound having an aliphatic unsaturated bond which includes reacting a compound having an aliphatic unsaturated bond represented by the following general formula (1) with bromine:

$$R^1\text{—}O\text{—}Ar^1\text{—}Y\text{—}Ar^2\text{—}O\text{—}R^2 \qquad (1)$$

to produce a bromine compound represented by the following formula (2):

$$R^3\text{—}O\text{—}Ar^1\text{—}Y\text{—}Ar^2\text{—}O\text{—}R^4 \qquad (2)$$

wherein $Ar^1$, $Ar^2$ and Y are the same as defined in the above general formula (1), and $R^3$ and $R^4$ are groups obtained by saturating the unsaturated groups of $R^1$ and $R^2$ in the above general formula (1) with bromine, respectively.

The reaction is carried out in the presence of a solvent which is inactive in the reaction, and a substantial amount of the heat of reaction is removed from a reaction system by the vaporization of the solvent or bromine. A high-purity bromine compound in high yield which is useful as flame retardant, can be obtained.

18 Claims, 2 Drawing Sheets

BROMINE COMPOUND PRODUCTION METHOD

BACKGROUND OF THE INVENTION

1. Field of the Invention

The present invention relates to a method of producing a bromine compound by brominating a compound having an aliphatic unsaturated bond. More specifically, it relates to a method of producing a high-purity bromine compound from a compound having an aliphatic unsaturated bond industrially advantageously.

2. Prior Art

Generally speaking, the bromination reaction of an aliphatic unsaturated group is frequently used for the synthesis of brominated derivatives in the field of organic chemistry. However, reaction heat must be removed from a reaction system because heat generated by the reaction is strong. Therefore, the operation of adding bromine little by little in a mild condition by cooling the reaction system is generally employed.

For instance. JP-B 49-39655 (the term "JP-B" as used herein means an "examined Japanese patent publication") discloses a method of producing β,γ-dibromopropylbenzene and teaches that a reaction is carried out at a low temperature at which a secondary reaction does not occur when bromine is added.

JP-A 55-111429 (the term "JP-A" as used herein means an "unexamined published Japanese patent application") discloses that a diallyl ether obtained from 2,2-bis{(4-hydroxy-3,5-dibromo)phenyl}propane and allyl chloride is brominated in a halogenated aromatic hydrocarbon as solvent, teaches that this bromination is carried out at a temperature of 10 to 30° C., particularly 15 to 25° C. and specifies in Examples that bromine is added at a temperature of about 20° C. under cooling.

JP-A 50-30853 discloses a solid recovery method and teaches that bromine is added dropwise at a temperature of 20° C. or lower to carry out a reaction between the bromine and 2,2-bis{(3,5-dibromo-4-allyloxy)phenyl}propane in Examples.

JP-A 7-173092 teaches that bromine is added dropwise at a reaction temperature of 10 to 20° C. in 1 hour to carry out a reaction between the bromine and 2,2-bis{(3,5-dibromo-4-allyloxy)phenyl}propane so as to obtain a 2,3-dibromopropyl compound.

Further, JP-A 7-316087 discloses as an example that bromine is added dropwise to a methylene chloride solution of 2,2-bis{(3,5-dibromo-4-allyloxy)phenyl}propane in 1 hour while the reaction temperature is controlled to 24 to 27° C. by using a cooling pipe.

Meanwhile, JP-B 50-23693, for example, disclose as an example that bromine is reacted with bis{(3,5-dibromo-4-allyloxy)phenyl}sulfone at the boiling point of methylene chloride by dissolving the compound in methylene chloride in the bromination of bis{(3,5-dibromo-4-allyloxy)phenyl}sulfone.

JP-A 3-271267 and JP-A 4-234354 disclose the bromination of bis{(3,5-dibromo-4-allyloxy)phenyl}sulfone and teach that bromine is added to a methylene chloride solution of the above compound at 39° C. or 40° C. in 1 hour and at 35 to 39° C. in 1.5 hours, respectively. In these methods, the reaction is carried out in a reactor having a cooling pipe.

In all of the methods disclosed by these publications, the reaction is a small-scale laboratory-level reaction, a flask is frequently used as a reactor, and reaction heat is removed by cooling the reactor itself in most cases. These publications disclose conditions and means for carrying out the laboratory level reaction but not concrete conditions and means for removing a large amount of generated reaction heat effectively and for obtaining a high-purity bromine compound at a high yield on an industrial scale.

To carry out the bromination of a compound having an aliphatic unsaturated bond, particularly to carry out the introduction of many bromine atoms on an industrial scale, a large amount of generated reaction heat must be removed effectively. The development of means and an apparatus for this is desired. When reaction heat is not removed effectively, bromine must be supplied little by little and hence, the reaction time is prolonged, resulting in lowered yield and purity.

SUMMARY OF THE INVENTION

In view of the above situation, the inventors of the present invention have conducted intensive studies to provide a method of producing a high-purity bromine compound on an industrial scale by reacting a compound having an aliphatic unsaturated bond with bromine efficiently and have found that a high-purity bromine compound can be produced at a high yield without causing a secondary reaction by removing the substantial amount of reaction heat generated by bromination from a reaction system by the vaporization heat of a solvent or bromine when bromination is carried out by reacting the compound having an aliphatic unsaturated bond with bromine in the presence of the solvent which is inactive in a reaction. The present invention has been accomplished by this finding.

That is, according to the present invention, there is provided a bromine compound production method comprising reacting a compound having an aliphatic unsaturated bond represented by the following general formula (1) with bromine:

$$R^1-O-Ar^1-Y-Ar^2-O-R^2 \qquad (1)$$

wherein $Ar^1$ and $Ar^2$ may be the same or different and are each an aromatic hydrocarbon group having 5 to 16 carbon atoms or saturated alicyclic hydrocarbon group having 5 to 12 carbon atoms, these hydrocarbon groups may be substituted by at least one halogen atom; Y is a saturated hydrocarbon group having 1 to 6 carbon atoms, sulfone group, sulfide group, ketone group, alkylene oxide group having 2 to 6 carbon atoms or single bond; $R^1$ and $R^2$ may be the same or different and are each a hydrocarbon group having 2 to 11 carbon atoms having at least one aliphatic unsaturated group, but, part of the unsaturated group of either one of them may be added by a halogen atom, to produce a bromine compound represented by the following general formula (2):

$$R^3-O-Ar^1-Y-Ar^2-O-R^4 \qquad (2)$$

wherein $Ar^1$, $Ar^2$ and Y are the same as defined in the above general formula (1), and $R^3$ and $R^4$ are groups obtained by saturating the unsaturated groups of $R^1$ and $R^2$ in the above general formula (1) with a bromine atom, respectively, wherein the reaction is carried out in the presence of a solvent which is inactive in a reaction, and the substantial amount of reaction heat is removed from a reaction system by the vaporization heat of the solvent or bromine.

The bromine compound production method according to the present invention will be described in detail and more specifically hereinunder.

The compound having an aliphatic unsaturated bond used in the method of the present invention is represented by the above general formula (1). In the general formula (1), $Ar^1$ and $Ar^2$ may be the same or different and are each an aromatic hydrocarbon group having 5 to 16 carbon atoms, preferably 6 to 12 carbon atoms, or a saturated alicyclic hydrocarbon group having 5 to 12 carbon atoms, preferably 6 to 10 carbon atoms. It is industrially advantageous that $Ar^1$ and $Ar^2$ should be the same and an aromatic hydrocarbon group. Illustrative examples of $Ar^1$ and $Ar^2$ include 1,4-phenylene group, 1,4-methylphenylene group, 1,4-dimethylphenylene group, 2,6-naphthylene group and 2,7-naphthylene group, out of which 1,4-phenylene group is preferred.

The carbon atom forming the hydrocarbon represented by $Ar^1$ and $Ar^2$ may be substituted by a halogen atom. To produce a flame retardant in particular, it is preferred that the carbon atom should be substituted by a halogen atom, particularly a bromine atom. The number of halogen atoms substituting the carbon atoms of each of $Ar^1$ and $Ar^2$ is 1 to 6, preferably 2 to 4.

In the general formula (1), Y is a group or bond for connecting $Ar^1$ and $Ar^2$ and selected from a saturated hydrocarbon group having 1 to 6 carbon atoms, preferably 1 to 3 carbon atoms, sulfone group (—$SO_2$—), sulfide group (—S—), ketone group (—CO—), alkylene oxide group having 2 to 6 carbon atoms, preferably 2 to 4 carbon atoms, and single bond. Y is preferably a methylene group, isopropylidene group, cyclohexylidene group, sulfide group, sulfone group, ketone group or single bond.

In the general formula (1), $R^1$ and $R^2$ may be the same or different and are each a hydrocarbon group having 2 to 11 carbon atoms, preferably 2 to 5 carbon atoms and at least one aliphatic unsaturated group. Part of the unsaturated group of either one of $R^1$ and $R^2$ may be substituted and saturated with a halogen atom, preferably bromine atom. Preferred examples of $R^1$ and $R^2$ include vinyl group, allyl group and isobutenyl group.

Illustrative examples of the compound having an aliphatic unsaturated bond represented by the general formula (1) include 2,2-bis{(3,5-dibromo-4-allyloxy)phenyl}propane, 2,2-bis{(3,5-dibromo-4-isobutenyloxy)phenyl}propane, bis{(3,5-dibromo-4-allyloxy)phenyl}methane, bis{(3,5-dibromo-4-isobutenyloxy)phenyl}methane, (3,3',5,5'-tetrabromo-4,4'-diallyloxy)biphenyl, (3,3',5,5'-tetrabromo-4,4'-divinyloxy)biphenyl, bis{(3,5-dibromo-4-allyloxy)phenyl}sulfone, bis{(3,5-dibromo-4-isobutenyloxy)phenyl}sulfone and the like. Out of these, 2,2-bis{(3,5-dibromo-4-allyloxy)phenyl}propane, 2,2-bis{(3,5-dibromo-4-isobutenyloxy)phenyl}propane, bis{(3,5-dibromo-4-allyloxy)phenyl}methane, bis{(3,5-dibromo-4-isobutenyloxy)phenyl}methane, (3,3',5,5'-tetrabromo-4,4'-diallyloxy)biphenyl and (3,3',5,5'-tetrabromo-4,4'-divinyloxy)biphenyl are preferred, 2,2-bis{(3,5-dibromo-4-allyloxy)phenyl}propane, 2,2-bis{(3,5-dibromo-4-isobutenyloxy)phenyl}propane, bis{(3,5-dibromo-4-allyloxy)phenyl}methane and bis{(3,5-dibromo-4-isobutenyloxy)phenyl}methane are more preferred, and 2,2-bis{(3,5-dibromo-4-allyloxy)phenyl}propane is particularly preferred.

The reaction between the compound having an aliphatic unsaturated bond and bromine is carried out in the presence of a solvent in the method of the present invention. The solvent must not exert a bad influence upon the reaction and be inactive. The solvent preferably has high solvent power for the compound having an aliphatic unsaturated bond but may dissolve part of the compound. Preferably, the solvent substantially dissolves a bromine compound produced by the bromination reaction of the compound having an aliphatic unsaturated bond.

The solvent in the present invention is used not only as a solvent for carrying out a reaction uniformly but also as a solvent for removing reaction heat from a reaction system. Therefore, a solvent having a boiling point at normal pressure of 0 to 100° C., preferably 20 to 90° C., is advantageous. Particularly when reaction heat is to be substantially removed by the vaporization heat of a solvent, it is desired that the solvent should have a boiling point at normal pressure of 20 to 80° C., particularly preferably 20 to 60° C.

Illustrative examples of the solvent include halogenated hydrocarbon such as methylene chloride, chloroform, 1,2-dichloroethane, 1,1-dichloroethane, bromoethane, butylchloride and chloropropane, ether-based hydrocarbon compounds such as diethyl ether, ethyl isopropyl ether, tetrahydrofuran and dioxane, aromatic hydrocarbon compounds such as benzene, carbon disulfide, pentane and the like. Bromine can be used as a solvent.

Out of these solvents, halogenated hydrocarbon are preferred, and methylene chloride and chloroform are particularly preferred. These solvents may be used alone or in admixture of two or more. These halogenated hydrocarbon may be used as a mixed solvent with dioxane.

The solvent is used in an amount of 2 to 1000 molecules, preferably 2.5 to 800 molecules, based on 1 unsaturated group of the compound represented by the above general formula (1). Since the substantial amount of reaction heat is removed from a reaction system by the vaporization heat of the solvent according to a preferred aspect of the present invention, it is advantageous to use the solvent in an amount of more preferably 3 to 700 molecules, particularly preferably 4 to 600 molecules.

Since the method of the present invention is characterized in that reaction heat is removed by the vaporization heat of the solvent or bromine, the solvent or bromine may be existent in a reaction system in such an amount that can provide vaporization heat corresponding to the reaction heat. However, as bromine involves in the reaction, it is reasonable and advantageous that the vaporization heat of the solvent should be used to remove the reaction heat.

As for the amount of bromine used in the method of the present invention, the ratio of bromine to the compound having an aliphatic unsaturated bond must be sufficient to obtain a desired bromine compound. That is, the number of bromine molecules based on 1 unsaturated group of the compound having an aliphatic unsaturated bond is preferably 1 to 5, more preferably 1.1 to 3.

In the method of the present invention, bromine itself or a bromine solution is used. A solvent to be used in the bromine solution is the same as the above solvent and the concentration of bromine is preferably 10 to 90 wt %.

In the method of the present invention, the compound having an aliphatic unsaturated bond is reacted with bromine by mixing bromine or a bromine solution with a solution of the compound having an aliphatic unsaturated bond dissolved in a solvent which is inactive with bromine. It is mandatory to remove the substantial amount of the reaction heat of bromination by the vaporization heat of the solvent or bromine during this bromination reaction. The substantial amount of reaction heat means 80% or more, preferably 85% or more, of the theoretical amount of heat generated by a desired bromination reaction.

The reaction temperature of the bromination reaction of the present invention is not particularly limited. Any reaction temperature is acceptable if the substantial amount of the reaction heat of bromination is removed by the vaporization heat of bromine or a solvent as described above. The bromination reaction can be carried out not only at normal pressure but also at an increased pressure or a reduced pressure. The reaction temperature is preferably 0° C. or higher, more preferably 5° C. or higher. When the boiling point of the solvent used is lower than the boiling point of bromine, the reaction temperature can be elevated by increasing pressure and when the boiling point of the solvent used is higher than the boiling point of bromine, the reaction temperature can be lowered by reducing pressure.

Thus, the reaction temperature of the present invention can be controlled by operating pressure according to the type (boiling point) of the solvent used and the amount of bromine. The reaction temperature is generally 0 to 60° C., preferably 5 to 55° C., particularly preferably 10 to 50° C.

In the method of the present invention, the substantial amount of the reaction heat of bromination is removed by the vaporization heat of a solvent or bromine during the bromination reaction. A reflux condenser or the like installed in the upper portion of a reactor is preferably used to cool and liquefy vapor produced by vaporization and recycle it to a reaction system, that is, reflux the vapor because of easy operation. The removal of reaction heat by vaporization can be carried out without using a reflux condenser. This method will be described hereinafter.

By removing the substantial amount of the reaction heat of bromination by the vaporization heat of the solvent or bromine, the purity of the produced bromine compound is increased. A by-product is more readily produced when the compound having an aliphatic unsaturated bond is simply reacted with bromine at a high temperature than at a low temperature, thereby reducing purity. However, in the method of the present invention, a high-purity bromine compound can be obtained probably because the compound having an aliphatic unsaturated bond and bromine are uniformly dispersed in the solution by a stirring effect which is obtained when the solvent or bromine is vaporized and thereby a secondary reaction hardly occurs.

In the method of the present invention, a method of mixing a solution of the compound having an aliphatic unsaturated bond dissolved in the inactive solvent with bromine or a bromine solution is not particularly limited. Bromine or a bromine solution may be added to a solution of the compound having an aliphatic unsaturated bond and mixed, a solution of the compound having an aliphatic unsaturated bond may be added to bromine or a bromine solution and mixed, or bromine or a bromine solution and a solution of the compound having an aliphatic unsaturated bond may be added to a reactor simultaneously and mixed together.

In the method of the present invention, a reaction between the compound having an aliphatic unsaturated bond and bromine must be carried out in the presence of the solvent which is inactive in a reaction and the substantial amount of reaction heat must be removed from a reaction system by the vaporization heat of the solvent or bromine. For this purpose, it is desired to adopt conditions and means for effectively discharging a large amount of generated reaction heat from the reaction system by the vaporization of the solvent or bromine as the vapor of the solvent or bromine. These conditions and means will be described in detail and more specifically hereinafter. When the solvent contacts reaction elements uniformly, the vaporization of the solvent and bromine is effectively carried out, and reaction heat is removed from the reaction system smoothly, the reaction can be completed quickly and a high-purity bromine compound can be obtained advantageously. Therefore, preferred results can be obtained by employing means of mixing a reaction mixture contained in the reaction system completely.

Accordingly, it is industrially advantageous to select the type and amount of the solvent, the amount of bromine and reaction temperature from the above ranges. Further, it has been found that the existence of water in the reaction system and the addition of an alcohol have an influence upon the purity and quality of the obtained bromine compound. This will be described hereinafter.

In the reaction of the present invention, impurities contained in the reaction solution become an important factor of carrying out the bromination reaction of the present invention efficiently and obtaining a high-purity bromine compound at a high yield. Particularly, water contained in the reaction solution reacts with bromine to form an active intermediate which causes a reaction with an aliphatic unsaturated bond competitively. Therefore, great care must be taken of the existence of water in the compound having an aliphatic unsaturated bond, bromine and the solvent to carry out a reaction, and the existence of water must be avoided basically. Accordingly, as for the concentration of water, the number of water molecules is preferably 10 or less, more preferably 0.05 to 10, much more preferably 0.05 to 5 based on 100 unsaturated groups of the compound having an aliphatic unsaturated bond. When the concentration of water is high, the obtained bromine compound has low purity and is a solid having no storage stability which is sticky disadvantageously. The water content is measured by the Karl Fischer's method.

The concentration of water contained in the reaction solution can be reduced to a certain degree by removing water contained in the compound having an aliphatic unsaturated bond, bromine and the solvent. However, when a reaction is carried out on an industrial scale, it is extremely difficult to prevent entry of water into the reaction system due to restrictions from the apparatus and operation. To cope with this, the present inventors have conducted studies on a method for preventing a bad influence upon the handling and use of the obtained bromine compound even when a slight amount of water is existent in the reaction system and have found that the addition of a specific alcohol to the reaction system is effective.

The alcohol to be added to the reaction system is represented by the following general formula (3).

$$R^5-(OH)_n \qquad (3)$$

wherein $R^5$ is an aliphatic group having 1 to 6 carbon atoms and a valence of n, and n is an integer of 1 to 4.

In the above general formula (3), $R^5$ is an aliphatic group having a valence of 1 to 4 and 1 to 6 carbon atoms, preferably an aliphatic hydrocarbon group having 1 to 6 carbon atoms, oxygen-containing saturated hydrocarbon group having 1 to 4 carbon atoms or a sulfur-containing saturated hydrocarbon group having 1 to 4 carbon atoms. n is an integer of 1 to 4, preferably 1 or 2. Illustrative examples of the alcohol represented by the general formula (3) include methanol, ethanol, n-propanol, i-propanol, n-butanol, i-butanol, sec-butanol, tert-butanol, ally alcohol, ethylene glycol, diethylene glycol and the like. Out of these, methanol, ethanol, n-propanol, i-propanol, n-butanol, i-butanol, sec-butanol and tert-butanol are preferred, and methanol, ethanol and i-propanol are particularly preferred.

The alcohol is used in an amount equivalent to 0.5 to 20 hydroxyl groups, preferably 0.8 to 18 hydroxyl groups, more preferably 1 to 15 hydroxyl groups, particularly preferably 1 to 10 hydroxyl groups based on 100 unsaturated groups of the compound having an aliphatic unsaturated bond. When the amount of the alcohol is equivalent to less than 0.5 hydroxyl group based on 100 unsaturated groups of the compound having an aliphatic unsaturated bond, a reaction between the compound having an aliphatic unsaturated bond and an active intermediate produced by a reaction between water and bromine readily proceeds, thereby reducing the thermal stability of the obtained bromine compound disadvantageously. When the amount of the alcohol is equivalent to more than 20 hydroxyl groups based on 100 unsaturated groups, the amount of a by-product produced by a reaction between an intermediate produced by a reaction between the alcohol and bromine and the compound having an aliphatic unsaturated bond increases, thereby reducing the purity of the obtained bromine compound. When this bromine compound is blended into a resin as a flame retardant, it exerts a bad influence upon the flame retardancy of the resulting resin composition disadvantageously.

In the bromination reaction of the present invention, the formation of a by-product derived from water is suppressed by causing the alcohol represented by the general formula (3) to be existent in a solution prepared by mixing a solution of the compound having an aliphatic unsaturated bond with bromine or a bromine solution as described above. However, when the amount of water existent in the mixture solution is too large, a large amount of the compound having a hydroxyl group must be used to suppress a secondary reaction derived from water. Therefore, as described above, a by-product produced by a reaction between the compound having an aliphatic unsaturated bond and an intermediate produced by a reaction between the alcohol and bromine is produced in large quantities, whereby the purity of the obtained bromine compound becomes insufficient, which exerts a bad influence upon the flame retardancy of a resin composition obtained by blending this bromine compound as a flame retardant into a resin. Accordingly, the concentration of water in the reaction solution essentially composed of a solution of the compound having an aliphatic unsaturated bond, bromine or bromine solution and a compound having a hydroxyl group at the time of a bromination reaction is preferably equivalent to 10 or less water molecules, more preferably 0.05 to 10 water molecules, much more preferably 0.05 to 5 water molecules based on 100 unsaturated groups of the compound having an aliphatic unsaturated bond.

The method of the present invention may be carried out in accordance with a batch, semi-batch or continuous process as long as the substantial amount of reaction heat is removed from the reaction system by the vaporization heat of the solvent or bromine, preferably most of reaction heat is removed from the reaction system by the vaporization heat of the solvent. To simplify an explanation, batch and continuous processes will be described hereinafter. Partial modification and alternation of these are permitted as far as they do not impair the essential feature of the present invention. Particularly, the semi-batch process can be easily employed by one of the ordinary skill in the art from descriptions of the batch and continuous processes as a known combination thereof.

In the following description, descriptions of the control of water contained in the reaction system and the addition of an alcohol are omitted. Particularly, when an alcohol is added, it may be added alone or may be added to the compound having an aliphatic unsaturated bond, bromine or the solvent, or a mixture thereof.

In the following description, the compound having an aliphatic unsaturated group is simply referred to as "unsaturated compound" and the solvent which is inactive in a reaction is simply referred to as "solvent".

I. batch process:

In this batch process, the unsaturated compound, bromine and the solvent are placed in a reactor in a desired order, a reaction and the removal of reaction heat are carried out in the reactor, and the reaction mixture is not substantially removed before the end of the reaction. This batch process is further divided into the following processes (I-a) to (I-d).

process (I-a):

In this process (I-a), the unsaturated compound, bromine and the solvent are supplied into a reactor separately at the same time or as a mixture. In this process (I-a), it is desired to supply the unsaturated compound, bromine and the solvent into the reactor in almost the same ratio as described above. The solvent may be added as a solution of the unsaturated compound or a solution of bromine. When the solvent is added as a solution of the unsaturated compound and/or a solution of bromine, it may be further added alone as a supplement, or part thereof may be charged into the reactor in advance.

As the reaction of the present invention is desirably such that the unsaturated compound, bromine and the solvent should be uniformly and effectively contacted to one another as described above, a reactor equipped with a stirrer is used. Further, a reactor equipped with a reflux condenser installed in the upper portion which is used to reflux the solvent and bromine vaporized by reaction heat to the reaction system is advantageous. A reactor equipped with a stirrer and a reflux condenser is advantageously used in any of the following processes.

It is particularly preferred to mix the unsaturated compound, bromine and the solvent completely using a flow mixer, particularly a static mixer, and supply the resulting mixture into the reactor in order to contact them uniformly in the reactor.

process (I-b):

In this process (I-b), the unsaturated compound or a solution thereof is supplied into a reactor filled with bromine or a bromine solution. In this process (I-b), the solvent is preferably added as a solution of bromine, the unsaturated compound or both. Part of the solvent may be further supplied alone as a supplement.

As a bromination reaction can be carried out in a short period of time and productivity is improved in this process (I-b), this process is industrially excellent. Since the bromination reaction itself completes in several tens of seconds, the time required from the start of the bromination reaction to the end of the reaction is generally several minutes.

As for how to add a solution of the unsaturated compound to bromine or a bromine solution, the solution of the unsaturated compound is added at a rate of 0.4 to 1,000 mmol/sec, more preferably 0.4 to 300 mmol/sec, more preferably 0.5 to 100 mmol/sec in terms of the unsaturated compound based on 1 mol of bromine.

process (I-c):

In this process (I-c), the unsaturated compound and bromine are supplied into a reactor filled with the solvent separately. In this process (I-c), the unsaturated compound is supplied as a solution of the solvent. Bromine can also be supplied as a solution. In this process, the ratio of the unsaturated compound, bromine and the solvent is substantially the same as described above.

process (I-d):

In this process (I-d), bromine or a bromine solution is supplied into a reactor filled with the unsaturated compound or a solution thereof. In this process (I-d), the solvent is preferably added to a solution of the unsaturated compound, a bromine solution, or both. Part of the solvent may be supplied alone as a supplement.

How to add bromine or a bromine solution to the solution of the unsaturated solution in the reactor in this process (I-d) will be detailed hereinunder. That is, bromine or a bromine solution is added at a rate of 0.4 mmol/sec or more, preferably 0.5 mmol/sec or more, more preferably 1 mmol/sec or more, particularly preferably 1.5 mmol/sec or more and at a rate of 1,000 mmol/sec or less, preferably 300 mmol/sec or less, more preferably 100 mmol/sec or less, much more preferably 50 mmol/sec, particularly preferably 20 mmol/sec or less in terms of bromine based on 1 mol of the unsaturated compound. When the addition rate of bromine or a bromine solution is too low, productivity may lower disadvantageously and when the addition rate is to high, the reaction may not be controlled disadvantageously.

The product of the addition rate (mmol/sec) of bromine to 1 mol of the unsaturated compound and the concentration (mol/l) of a solution of the unsaturated compound dissolved in the solvent is preferably 0.7 or more, more preferably 0.7 to 200, particularly preferably 0.7 to 100. When the value of this product is smaller than 0.7, the concentration of the solution of the unsaturated compound greatly lowers, thereby reducing production efficiency disadvantageously.

Out of the above batch processes, processes (I-a), (I-b) are (I-c) are industrially preferred, processes (I-b) and (I-c) are more preferred from the viewpoint of the quality and purity of the obtained bromine compound.

II. continuous process:

The present inventors have conducted further studies and have found that the above production technology of a bromine compound in which the substantial amount of reaction heat is removed from a reaction system by the vaporization heat of the solvent or bromine makes it possible to obtain a high-purity bromine compound efficiently in a short reaction time using a simple and very compact reactor and a continuous process which will be described hereinafter.

That is, according to the present invention, there is provided a continuous bromine compound production method comprising reacting a compound having an aliphatic unsaturated bond represented by the above general formula (1) with bromine to produce a bromine compound represented by the above general formula (2), wherein the method comprises the steps of continuously supplying the compound represented by the general formula (1), bromine and a solvent which is inactive in a reaction into a reactor separately or as a mixture of a desired combination thereof in such a ratio that the number of bromine molecules based on 1 unsaturated group of the compound represented by the general formula (1) is 1 to 5, and reacting them with each other while the substantial amount of reaction heat is removed by the vaporization heat of the solvent or bromine in the reactor, taking out a reaction mixture from the reactor, and recovering the bromine compound represented by the above general formula (2) from the reaction mixture.

In the continuous process of the present invention, the compound represented by the above general formula (1), bromine and the solvent which is inactive in a reaction are continuously supplied separately or as a mixture of a desired combination thereof. Since the compound (unsaturated compound) represented by the above general formula (1) and bromine are reacted with each other quickly when they are contacted to each other, a mixture of the compound and bromine should not be supplied into the reactor.

To carry out the continuous process, the unsaturated compound, bromine and the solvent can be supplied into the reactor in the following ways (i) to (iii).

(i) to supply a solution of the unsaturated compound and bromine separately.
(ii) to supply a solution of the unsaturated compound and a bromine solution separately.
(iii) to supply the unsaturated compound, bromine and the solvent separately.

The above (i) to (iii) are for explaining combinations of means of supplying the unsaturated compound, bromine and the solvent which are required to carry out the continuous process of the present invention. Partial modifications of these are included in the scope of the present invention as a matter of course. When there is another component to be added, the component may be added independently or may be added as a solution of the solvent or to a solution of the unsaturated compound or a bromine solution. The alcohol represented by the above general formula is also a component to be added.

The ratio of the unsaturated compound, bromine and the solvent which is inactive in a reaction to be supplied into the reactor is substantially not different from the above ratio. That is, the solvent is used in an amount of at least 2 molecules, preferably at least 2.5 molecules, more preferably at least 3 molecules, the most preferably at least 4 molecules based on 1 unsaturated group of the unsaturated compound.

The above upper limit is restricted from an economical point of view and generally 1000 molecules or less, preferably 800 molecules or less, more preferably 700 mloecules or less, the most preferably 600 molecules or less.

Bromine is used in a number of bromine molecules of 1 to 5, preferably 1.1 to 3 based on 1 unsaturated group of the unsaturated compound. The range of 1.2 to 3 is particularly advantageous from an industrial point of view.

In the continuous process of the present invention, it is important to keep the number of bromine molecules contained in the reaction solution in the reactor within the range of 1 or more, preferably 1 to 5, more preferably 1.1 to 3 based on 1 aliphatic unsaturated group of the unsaturated compound. To obtain a high-purity and high-quality bromine compound, the amount of bromine in the reaction solution must be always kept within that range during a reaction. If the amount of bromine falls below the above range instantaneously (in the order of several seconds), there will be no trouble but the substantial reaction time and the amount of bromine should be kept within the above ranges. If the amount of bromine is kept below the above range for a long time, the unsaturated group of the unsaturated compound causes a secondary reaction, thereby producing an undesired secondary reaction product and reducing the purity of the bromine compound of interest. It is considered that this secondary reaction is mainly caused by a reaction between the unsaturated group and an active intermediate formed by a reaction between water contained in the reaction solution and bromine.

In the continuous process, to keep the amount of bromine contained in the reaction solution within the range of 1 molecule or more, preferably 1.1 molecle or more based on 1 unsaturated group of the unsaturated compound, the ratio of the unsaturated compound and bromine supplied into the reactor may be always kept within the above range.

A bromination reaction occurs quickly in the reactor, and generated reaction heat must be removed by the vaporization of the solvent or bromine. A reflux conenser installed in the upper portion of the reactor is preferably used to cool and liquefy the vapor of the vaporized solvent or bromine and return it to the reaction solution, that is, reflux the solvent or bromine because of easy operation. By removing the reaction heat of bromination by the vaporization heat of the solvent or bromine, the purity of the produced bromine compound is increased. A by-product is more readily produced when the unsaturated compound is simply reacted with bromine at a high temperature than at a low temperature, thereby reducing purity. However, in the method of the present invention, a high-purity bromine compound can be obtained probably because the unsaturated compound and bromine are uniformly dispersed in the solution by a stirring effect obtained by refluxing and thereby a secondary reaction hardly occurs.

When the amount of the added solution of the unsaturated compound dissolved in the solvent is represented by A (1/min), the amount of the added bromine or bromine solution is represented by B (1/min) and the amount of the reaction solution in the reactor is represented by C (1), a bromination reaction is preferably carried out to ensure that the residence time represented by the following equation should be 0.1 to 200 minutes, preferably 0.2 to 100 minutes.

$$\text{residence time (min)} = C(1)/\{A(1/\text{min}) + B(1/\text{min})\}$$

Strictly speaking, the total of the amount of the added solution of the unsaturated compound dissolved in the solvent (1/min) and the amount of the added bromine or bromine solution (1/min) differs from the amount of the reaction solution output from the reactor. However, the amount of the added bromine (1/min) is much smaller than the amount of the added solution of the unsaturated compound dissolved in the solvent and a volume change caused by a reaction can be almost ignored. Since the amount of the solvent scattered to the outside of the reactor is very small, the total of the amount of the added solution of the unsaturated compound dissolved in the solvent (1/min) and the amount of the added bromine or the bromine solution (1/min) is approximate to the amount of the reaction solution output from the reactor.

Since recycling of part of the reaction solution to the reactor makes it possible to make the reactor more compact and improve reaction efficiency, it is advantageously used. The method of recycling is not particularly limited and another circulation pipe may be provided in the reactor separately from the output port of the reaction solution, or part of the output reaction solution can be recycled to the reactor.

The recycled reaction solution may be added to the reactor directly, or mixed with the solution of the unsaturated compound, bromine or the bromine solution, or a mixture solution thereof and added to the reactor as a mixture.

Since a short-time bromination reaction is possible and productivity is improved in the continuous process of the present invention, the above recycling method is preferred. The bromination reaction itself almost completes in several tens of seconds and the above range of the residence time suffices The reaction temperature of the bromination reaction of the present invention is a temperature at which the reaction heat of bromination is removed by the vaporization heat of bromine or the solvent. The bromination reaction can be carried out not only at normal pressure but also at an increased pressure or a reduced pressure. The reaction temperature is preferably 0° C. to 60° C. as described above. When the boiling point of the solvent used is lower than the boiling point of bromine, the reaction temperature can be elevated by increasing pressure and when the boiling point of the solvent used is higher than the boiling point of bromine, the reaction temperature can be lowered by reducing pressure.

To carry out the continuous process of the present invention, the reactor is preferably equipped with a stirrer to contact the unsaturated compound, bromine and the solvent to one another uniformly and effectively and remove the substantial amount of reaction heat from the reactor by the vaporization of the solvent or bromine and with a reflux condenser installed in the upper portion to reflux the vaporized solvent or bromine advantageously.

According to studies conducted by the present inventors, it has been found that when the unsaturated compound and bromine and preferably at least part of the solvent are mixed together uniformly in a short period of time right before they are supplied into the reactor to carry out the continuous process of the present invention, the unsaturated compound, bromine and the solvent are contacted to one another uniformly in the reactor and the reaction heat of a bromination reaction can be removed by the vaporization of the solvent or bromine more effectively.

Mixing of the unsaturated compound and bromine right before they are supplied into the reactor (solvent may be further mixed) should be carried out uniformly in a short period of time. To this end, a flow mixer is used to mix them and supply them into the reactor as a mixture solution. The unsaturated compound and bromine are mixed in the flow mixer but part or all of the solvent is further mixed together.

The flow rate of the mixture solution in the flow mixer is 15 to 500 cm/sec, preferably 50 to 400 cm/sec so that mixing is carried out uniformly in a short period of time. The residence time of the mixture solution in the flow mixer is 0.01 to 180 sec, preferably 0.05 to 120 sec, more preferably 0.1 to 60 sec. A range of 0.1 to 20 sec is particularly recommended.

Any flow mixer is acceptable if it can mix a liquid mixed flow uniformly and effectively in a short period of time. A static mixer is particularly preferred. The static mixer having 4 to 20 elements, preferably 5 to 15 elements is advantageously used.

The static mixer is a well known apparatus for chemical engineering as a mixer or heat exchanger. The static mixer is a tubular type mixer available from Kenix of the U.S. and having no drive unit. The static mixer incorporates rectangular plates called "element" which are twisted at a right angle and arranged such that their cross sections cross each other at a right angle alternately.

In the continuous process of the present invention, when the unsaturated compound, bromine and the solvent are supplied continuously into the reactor, use of a flow mixer, particularly a static mixer, as means of supplying them is extremely effective in completing a bromination reaction in an extremely short period of time, suppressing a secondary reaction and obtaining a high-purity bromine compound.

The mixture solution mixed in the flow mixer is supplied into the reactor immediately. Since part of a bromination reaction starts in the solution mixed in the flow mixer and the residence time of the solution in the mixer is controlled to a short time, the mixture solution passing through the mixer is supplied into the reactor immediately. In the reactor, the solution is further stirred so that it is fully mixed. Stirring is preferably carried out using a stirrer but part of the solution may be circulated in the reactor.

The volume of the reactor is 30 times or more, preferably 50 times or more the volume of the mixer. The upper limit of the size of the reactor is not particularly limited. A volume 200,000 times or less the volume of the mixer is enough but a reactor having a volume more than 200,000 times the volume of the mixer is not preferred from an economical point of view. The reactor having such a large volume functions to suppress the scattering of the solvent and bromine by boiling by radiating in the reactor reaction heat generated during a reaction in the mixer and to complete a bromination reaction by promoting stirring and mixing.

At this point, means of removing the reaction heat of bromination by the vaporization heat of the solvent or bromine can be used. That is, a reflux condenser which is installed in the reactor to cool vapor produced by vaporization to liquefy it and return it to the reaction solution, that is, reflux the vapor is preferably used because of easy operation. This means is preferably used because the unsaturated compound and bromine are dispersed uniformly in the solution by a stirring effect obtained by refluxing, a secondary reaction hardly occurs, a high-purity bromine compound is easily obtained, and a bromination reaction proceeds stably while the reaction temperature is kept constant and without the scattering of the solvent or bromine.

III. separation and recovery of bromine compound

The bromine compound of interest can be separated and recovered from the reaction mixture obtained by the above bromination reaction by a method known per se. However, unreacted bromine remains in the reaction mixture, and the residual bromine is treated with a reducing agent to convert it into hydrobromic acid which is then neutralized with an alkaline neutralizing agent.

However, this method involves such problems that at least two reduction and neutralization steps are required, operation is complicated, and treatments take long.

To cope with this, the present inventors have improved a method for separating and recovering a bromine compound from the reaction mixture in a short period of time by simple means and have found that the residual bromine can be treated in a short period of time simply by mixing and reacting a reducing agent and an alkaline neutralizing agent with the residual bromine contained in the reaction mixture in amounts more than specific amounts at the same time.

In other words, they have found a method of adding 2 mols or more of a reducing agent and 2 mols or more of an alkaline neutralizing agent based on 1 mol of the residual bromine to the reaction solution after the completion of a reaction at the same time and mixing them. This method will be referred to as "treatment method" hereinafter.

The reducing agent used in this treatment method is a reducing agent which is used in a general reduction reaction, as exemplified by sodium hydrogen sulfite, sodium dithionite, sodium sulfite, oxalic acid, hydrogen sulfide, sodium nitrite, potassium nitrite, hydroxyamine sulfate, tin, stannous oxide, hydrazine and the like. Out of these, sodium hydrogen sulfite, sodium dithionite, sodium sulfite, oxalic acid and sodium nitrite are preferred. These reducing agents may be used as an aqueous solution. These reducing agents may be used alone or in admixture of two or more.

Illustrative examples of the alkaline neutralizing agent include alkali metal hydroxides, alkali metal carbonates, alkali earth metal hydroxides, alkali earth metal carbonates and the like Out of these, sodium hydroxide, potassium hydroxide, sodium carbonate, potassium carbonate, calcium hydroxide and calcium carbonate are preferred, and sodium hydroxide is particularly preferred. These alkaline neutralizing agents are preferably used as an aqueous solution. These alkaline neutralizing agents may be used alone or in admixture of two or more.

In the treatment method of the present invention, the reducing agent is added to the reaction mixture in an amount of 2 mols or more, preferably 2 to 30 mols, more preferably 2.2 to 15 mols, much more preferably 2.5 to 10 mols based on 1 mol of the residual bromine contained in the reaction mixture. When the amount of the added reducing agent is smaller than 2 mols, bromine remains in the mixture and a low-purity bromine compound which is colored brown is obtained disadvantageously. The alkaline neutralizing agent is added to the reaction mixture in an amount of 2 mols or more, preferably 2 to 50 mols, more preferably 2.2 to 30 mols, much more preferably 2.5 to 20 mols based on 1 mol of the residual bromine contained in the reaction mixture. When the amount of the added neutralizing agent is smaller than 2 mols, hydrogen bromide remains in the aqueous solution, this strong acid aqueous solution cannot be discarded directly, and part of hydrogen bromide remains in the mixture, readily corrodes a metal and has an irritating smell, which is not preferred for working environment.

The above reducing agent and the above alkaline neutralizing agent are added to the reaction mixture containing a bromine compound and bromine at the same time. Although the reducing agent and the neutralizing agent may be added separately or as a mixture, they are preferably added separately because the reducing agent does not cause a secondary reaction due to alkali. Adding these agents at the same time does not mean that they are added exactly at the same time but means that the addition of one of the agents is completed in at least 10 minutes, preferably 5 minutes after the addition of the other agent. As for how to add these, it is preferred to add the reducing agent first and then the neutralizing agent immediately.

In the treatment method, the reaction mixture containing the reducing agent and the neutralizing agent is mixed to carry out reduction and neutralization reactions smoothly. Various mixers can be used to mix these, such as agitation tanks for stirring by the rotation of agitating elements (in which the center line of the tank and the center line of the agitator shaft are aligned with each other, the agitator shaft is inclined, and the agitator shaft is provided on the side wall of the tank), stirring by rocking the tank, circulating a liquid in the tank by a pump and the like, and in-line mixers such as static mixers. Out of these, agitation tanks are preferred.

The weight ratio of the reaction mixture to a water phase at the time of carrying out reduction and neutralization reactions is preferably 20:80 to 80:20, more preferably 30:70 to 70:30, particularly preferably 40:60 to 60:40. Within this range, reduction and neutralization reactions proceed efficiently and bromine is removed in a short period of time. Therefore, water or the solvent is preferably added to the reaction mixture to ensure that the weight ratio should fall within the above range before reduction and neutralization reactions are carried.

The time required to carry out the reduction and neutralization reactions of bromine contained in the reaction mixture is preferably 2 minutes or more, more preferably 2 to 90 minutes, much more preferably 5 to 60 minutes, particularly preferably 10 to 45 minutes.

In the present invention, the number of times of washing with water is only one after the end of the reduction and neutralization reactions. Therefore, the number of operation steps for the reduction and neutralization reactions is reduced, thereby making easy process control.

The bromine compound of interest is recovered from the reaction mixture treated in accordance with the above method by a method known per se, for example, precipitation with a poor solvent.

The separation and recovery of the bromine compound of interest from the reaction mixture obtained by the above bromination reaction can be also carried out by reduction and neutralization treatments using a static mixer as will be described hereinafter.

In other words, this method is a method of reducing and treating bromine by mixing an aqueous solution of a reducing agent with a reaction mixture solution containing the bromine compound of interest and residual bromine, comprising the steps of introducing the solution containing the bromine compound and bromine and the aqueous solution of the reducing agent into a static mixer having 4 to 20 elements at a flow rate of the mixed solution of 5 cm/sec or more, mixing the solution for a residence time in the static mixer of less than 300 sec, charging the mixed solution output from the static mixer into an agitation tank having a volume 20 times or more the volume of the static mixer and neutralizing the reaction mixture.

The above listed reducing agents are used as the reducing agent used in this treatment method and the amount of the reducing agent is preferably 2 mols or more, more preferably 2 to 100 mols, much more preferably 2 to 50 mols, particularly preferably 2 to 20 mols based on 1 mol of the residual bromine. When the amount of the reducing agent is smaller than 2 mols, the reduction reaction becomes incomplete and bromine is liable to remain.

The reduction reaction of bromine must be carried out by mixing the reaction mixture with an aqueous solution of a reducing agent efficiently. Therefore, when an ordinary stirrer is used, its stirring efficiency is insufficient and the reduction reaction must be carried out in multiple stages to be completed. Then, when a static mixer is used as a mixer, mixing is carried out efficiently and bromine can be treated in a short period of time by a simple apparatus.

The condition for using a static mixer is that the substantial degree of mixing can be judged by the number of elements in the static mixer. It is considered that mixing is generally carried out by dividing all the elements into groups of 2 multiples, and the flow rate, viscosity, Reynolds number and the like of a liquid component in the static mixer are possible factors of mixing efficiency, out of which the flow rate is the most important. In the treatment method, the mixture solution of a reaction mixture and an aqueous solution of a reducing agent is introduced into a static mixer at a flow rate at the input port of the static mixer of 5 cm/sec or more, preferably 10 cm/sec or more. When the flow rate is lower than 5 cm/sec, the mixing efficiency is unsatisfactory and the reducing reaction is not carried out completely, Even when the mixture solution is introduced into the static mixer at a flow rate higher than 500 cm/sec, the mixing efficiency is not substantially different and a flow rate higher than that is not necessary. The flow rate is calculated from a calculation expression $(A+B)/C$ (cm/sec) when the addition rate of the reaction mixture to be introduced into the static mixer is represented by A (ml/sec), the addition rate of the aqueous solution of the reducing agent is represented by B (ml/sec) and the cross section of the static mixer is represented by C ($cm^2$).

The way of introducing the reaction mixture and the aqueous solution of the reducing agent into the static mixer is not particularly limited. A dropping funnel may be used to introduce them. Alternatively, a pump is preferably used to provide a desired flow rate so that a predetermined volume is supplied within a predetermined time by the pump.

The number of elements of the static mixer is 4 to 20. When the number of elements is 3 or less, mixing becomes insufficient and the obtained bromine compound has low purity. 21 or more elements are not necessary from the view point of mixing efficiency.

The residence time of the mixture solution of the reaction mixture and the aqueous solution of the reducing agent in the static mixer is 300 sec or less, preferably 0.001 to 300 sec, more preferably 0.005 to 180 sec, much more preferably 0.01 to 120 sec, still more preferably 0.05 to 60 sec, particularly preferably 0.1 to 10 sec. When the residence time is too long, it is difficult to separate the organic solvent phase from the water phase. The residence time is calculated from a calculation expression $X/(A+B)$ (sec) when the addition rate of the reaction mixture to be introduced into the static mixer is represented by A (ml/sec), the addition rate of the aqueous solution of the reducing agent is represented by B (ml/sec) and the inner volume of the static mixer is represented by X ($cm^3$).

In the above treatment method, the reaction mixture and the aqueous solution of the reducing agent which have been mixed in the static mixer are discharged from the static mixer, and this mixture solution is charged into an agitation tank having a volume 20 times or more the volume of the static mixer.

Although part of the reduction reaction proceeds by mixing the reaction mixture and the aqueous solution of the reducing agent in the static mixer, the mixture solution must be introduced into another agitation tank to further carry out the reduction reaction and radiate reaction heat in the static mixer. Any agitation tank is acceptable if it contains the solution mixed in the static mixer in a state of a mixture solution continuously and its agitation system is not particularly limited. For example, agitation systems for stirring by the rotation of agitating elements (in which the center line of the tank and the center line of the agitator shaft are aligned with each other, the agitator shaft is inclined, and the agitator shaft is provided on the side wall of the tank), stirring by rocking the tank, and circulating a liquid in the tank by a pump can be employed.

The volume of the agitation tank is 20 times or more, preferably 30 times or more, the volume of the static mixer. The upper limit of the size of the agitation tank is not particularly limited but an agitation tank having a volume 200,000 times or less the volume of the static mixer suffices. An agitation tank having more than 200,000 times is not preferred from an economical point of view. The agitation having such a large volume functions to complete the reduction reaction by stirring and mixing and to radiate in the agitation tank reaction heat produced by a reaction in the static mixer. A pipe is provided at the input port of the static mixer from the agitation tank to re-introduce the solution in the agitation tank into the static mixer.

The agitation time of the solution in the agitation tank is preferably 2 minutes or more, more preferably 2 to 90 minutes, much more preferably 3 to 60 minutes, particularly preferably 5 to 45 minutes. Stirring and mixing for that time completes the reduction reaction.

After the completion of the reduction reaction, bromine changes into hydrogen bromide most of which dissolves in the aqueous solution of the reducing agent to become acidic water having a relatively low pH. In this state, the bromine compound of interest may be recovered. Since the reactor is generally made from a metal and often causes safety problems such as corrosion and perforation by acid, it is preferred to neutralize the hydrogen bromide with an alkaline neutralizing agent.

In addition to the above listed alkaline neutralizing agents, for example, alkali metal hydroxides, alkali metal carbonates, alkali earth metal hydroxides, alkali earth meal carbonates and the like are used as the alkaline neutralizing agent. Out of these, sodium hydroxide, potassium hydroxide, sodium carbonate, potassium carbonate, calcium hydroxide and calcium carbonate are preferred, and sodium hydroxide is particularly preferred. These alkaline neutralizing agents are preferably used as an aqueous solution. These alkaline neutralizing agents may be used alone or in admixture of two or more.

The alkaline neutralizing agent is mixed with the solution after the end of the reduction reaction in an amount of 2 mols or more, preferably 2 to 100 mols, more preferably 2 to 50 mols, much more preferably 2 to 20 mols based on 1 mol of the residual bromine contained in the reaction mixture. At this point, the pH of the solution is preferably 7.5 or more, more preferably 8 or more. When the neutralizing agent is added in an amount of less than 2 mols, hydrogen bromide remains in the aqueous solution, this strong acid aqueous solution cannot be discarded directly, part of hydrogen bromide remains in the bromine compound, readily corrodes a metal and has an irritating smell, which is not preferred for working environment.

The time required for the neutralization reaction is preferably 2 minutes or more, more preferably 2 to 90 minutes, much more preferably 5 to 60 minutes, particularly preferably 10 to 45 minutes.

The bromine compound obtained by the method of the present invention is recovered by an appropriate method well known to one of the ordinary skill in the art, for example, precipitation with a poor solvent.

According to the method of the present invention, a bromine compound represented by the following general formula (2) and having high purity is obtained by the bromination reaction of an unsaturated compound represented by the above general formula (1) for saturating the unsaturated groups of the unsaturated compound with bromine atoms.

(2)

wherein $Ar^1$, $Ar^2$ and Y are the same as defined in the above general formula (1), and $R^3$ and $R^4$ are groups obtained by saturating the unsaturated groups of $R^1$ and $R^2$ in the above general formula (1) with bromine atoms, respectively.

The bromine compound obtained by the method of the present invention has a purity of 80 wt % or more, preferably 85 wt % or more, particularly preferably 90 wt % or more. The bromine compound having such high purity is extremely excellent as a flame retardant for thermoplastic resins.

The bromine compound obtained by the method of the present invention is excellent not only in purity but also in quality in terms of the content of impurities which exert a bad influence when it is used as a flame retardant.

That is, the obtained bromine compound contains a slight amount of a hydroxy bromine compound represented by the following formula (4):

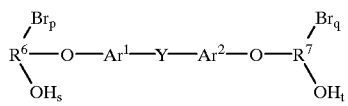

(4)

wherein $Ar^1$, $Ar^2$ and Y are the same as defined in the above general formula (1), $R^6$ and $R^7$ may be the same or different and are each a hydrocarbon group having 2 to 11 carbon atoms, p and q are each an integer of 0 to 10, provided that (p+q) is an integer of 1 or more, preferably 2 to 10, and s and t are each an integer of 0 to 5, provided that (s+t) is an integer of 1 or more, preferably 1 to 5.

The content of the hydroxy bromine compound represented by the above formula (4) contained in the bromine compound of the present invention is 0.02 mol or less, preferably 0.0001 to 0.02 mol, more preferably 0.0001 to 0.015 mol, particularly preferably 0.0001 to 0.01 mol based on 1 mol of the bromine compound represented by the above formula (1). When the content of the compound represented by the formula (4) is more than 0.02 mol based on 1 mol of the bromine compound represented by the formula (1), the thermal stability of the bromine compound of the present invention deteriorates disadvantageously. The compound represented by the formula (4) is a by-product produced by a reaction between the unsaturated compound and an intermediate produced by a reaction between bromine and water contained in the reaction solution which is essentially composed of a solution of the unsaturated compound, bromine or a bromine solution and an alcohol when the above unsaturated compound and bromine are reacted with each other to produce a bromine compound represented by the formula (1).

When the bromination reaction in the method of the present invention is carried out by the addition of an alcohol represented by the above general formula (3), the obtained bromine compound has high purity and contains a slight amount of an alkoxy bromine compound represented by the following general formula (5) which does not exert a bad influence upon thermal stability thereof.

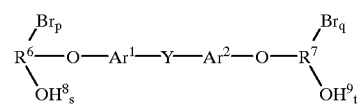

(5)

wherein $Ar^1$, $Ar^2$ and Y are the same as defined in the above general formula (1), $R^6$ and $R^7$ may be the same or different and are each a hydrocarbon group having 2 to 11 carbon atoms, p, q, s and t are the same as defined in the above general formula (4), and $R^8$ and $R^9$ are each an aliphatic group having 1 to 6 carbon atoms.

The compound represented by the formula (5) is a by-produced by a reaction between the aliphatic unsaturated group of the unsaturated compound and an intermediate produced by a reaction between bromine and an alcohol represented by the above formal (3) and does not exert a bad influence upon the thermal stability of the bromine compound. The content of the alkoxy bromine compound represented by the formula (5) is preferably 0.01 to 0.2 mol, more preferably 0.01 to 0.15 mol, much more preferably 0.01 to 0.1 mol, particularly preferably 0.01 to 0.05 mol based on 1 mol of the bromine compound represented by the formula (1). When the content of the alkoxy bromine compound represented by the formula (5) is lower than 0.2 mol based on 1 mol of the bromine compound represented by the formula (1), the alkoxy bromine compound does not exert a bad influence upon the flame retardancy of a resin composition prepared by blending the bromine compound into a resin as a flame retardant.

BRIEF DESCRIPTION OF THE DRAWINGS

In FIG. 1, each number has the following means
1 the surface of glass
2 sample
3 the horizontal surface

In FIG. 2 and FIG. 3, each number has the following means,
1 an input port of a raw material solution
2 an input port of bromine or bromine solution
3 a stirrer
4 a reflux condenser
5 a thermometer
6 a pump
7 an input port of recycling solution
8 an output port of reaction solution
9 reaction solution

EXAMPLES

The following examples are given to further illustrate the present invention. In the following examples, the compound having an aliphatic unsaturated bond represented by the general formula (1) may be referred to as "raw material". The purity, bromine content and specific gravity of the bromine compound were measured in accordance with the following methods.

(1) purity, impurities derived from water and impurities derived from hydroxyl group-containing compound of bromine compound;

The purity, impurities derived from water and impurities derived from a hydroxyl group-containing compound of a bromine compound were measured by high performance liquid chromatography ("HPLC":SCL-6B of Shimadzu Corporation) in accordance with a method for detecting the absorption of 280 nm. The purity of the bromine compound was calculated from the ratio of the peak area of the bromine compound to the total peak area of all elements obtained by this chromatography which is taken as 100. The contents of impurities derived from water and from the hydroxyl group-containing compound were also measured and calculated by the HPLC, and the value are based on 1 mol of the bromine compound.

(2) analysis of bromine content

A sample was heated together with fuming nitric acid in a closed container to be decomposed and the quantity of generated hydrobromic acid was determined in accordance with a measuring method using silver nitrate (Carius method).

(3) specific gravity

The specific gravity was measured at 20° C. using a glass pycnometer.

(4) analysis of water amount

The amount of water was obtained by the Karl Fischer's method using a gravimetric titration type water measuring instrument (Model CA-06 of Mitsubishi Chemical Corporation).

(5) inclination angle (70° C., after 4 hours of heating)

Figure 1:
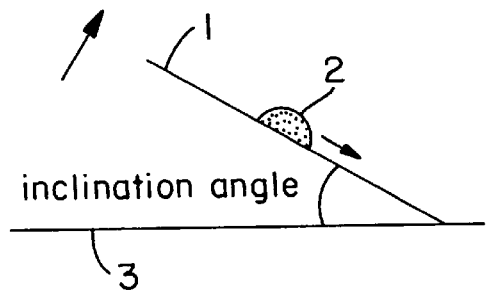
FIG. 1 is a diagram showing inclination angles in the evaluation of inclination angle (70° C., after 4 hours of heating)

After 0.5 g of a sample was placed in the center portion of a glass Petri dish (Pyrex glass of Iwaki Glass Co., Ltd.; center line average roughness of a bottom portion: 0.1 $\mu$m) and heated at 70° C. for 4 hours using a hot air circulation oven, the Petri dish was taken out and cooled to room temperature. This Petri dish was placed on a horizontal plane and inclined by lifting one end thereof while the other end is in contact with the horizontal plane. When the solid sample in the Petri dish slid, the inclination angle of the Petri dish from the horizontal plane when seen from the side was measured by a protractor (see FIG. 1). This inclination angle means the degree of agglomeration of the solid caused by the heat treatment. When the inclination angle is larger than 70°, the sample is unsatisfactory in terms of heat stability and easily causes a blocking phenomenon.

In the following examples and comparative examples, raw material Nos. (1) to (6) mean the following compounds.
No. (1); 2,2-bis{(3,5-dibromo-4-allyloxy)phenyl}propane
No. (2); 2,2-bis{(3,5-dibromo-4-isobutenyloxy)phenyl}propane
No. (3); bis{(3,5-dibromo-4-allyloxy)phenyl)methane
No. (4); bis{(3,5-dibromo-4-isobutenyloxy)phenyl}methane
No. (5); (3,3',5,5'-tetrabromo-4,4'-diallyloxy)biphenyl
No. (6); bis{(3,5-dibromo-4-isobutenyloxy)phenyl}sulfone
No. (7); bis{(3,5-dibromo-4-allyloxy)phenyl}sulfone

Example 1

135 g (0.216 mol) of 2,2-bis{(3,5-dibromo-4-allyloxy)phenyl}propane and 230 g of methylene chloride dehydrated by synthetic zeolite were charged into a 1 liter glass reactor equipped with a stirrer, reflux condenser, thermometer and dropping funnel (specific gravity of the solution: 1.47 and concentration calculated from this specific gravity: 0.87 mol/l). 72.7 g (0.455 mol) of bromine was added dropwise from the dropping funnel in 8 minutes while this solution was stirred and methylene chloride was refluxed at a temperature of 39 to 41° C.(addition rate of bromine; 4.4 m mol/sec. based on 1 mol of the raw material). After the end of addition, the reaction solution was kept stirred for 30 minutes while methylene chloride was refluxed at a temperature of 39 to 41° C. to terminate the addition reaction of bromine.

After excessive bromine contained in the reaction solution was reducted by 50 g of a 15 wt % aqueous solution of sodium bisulfite, generated hydrogen bromide was neutralized with a 25 wt % aqueous solution of sodium hydroxide. Thereafter, a methylene chloride layer was separated from this solution, and about 90% of methylene chloride was evaporated and thereafter, 500 ml of methanol was added to precipitate a reaction product, and the precipitate was filtered off to take out a bulk solid.

This bulk solid was ground with a mortar, and the ground product was dried at a temperature of 80° C. and a reduced pressure of 5 mmHg for 3 hours to obtain 198.5 g of a product (yield: 97.2%).

When the obtained product was analyzed by $^1$H-NMR, a signal derived from —CHBr— was observed at 4.51 to 4.53 ppm and a signal derived from —CH$_2$Br was observed at 3.94 to 4.09 ppm. It was confirmed from FT-IR analysis that the absorption of —O—CH$_2$— was observed and the absorption of an allyl group was not observed. It was confirmed from the results of the above analyses that the product was 2,2-bis{3,5-dibromo-4-(2,3-dibromopropyloxy)phenyl}propane. This bromine compound had a purity of 96.8%, a melting point of 110° C. and a bromine content of 67.5% (theoretical value: 67.8%).

Example 2

140.8 g (0.216 mol) of 2,2-bis{(3,5-dibromo-4-isobutenyloxy)phenyl}propane and a mixture solvent of 163 g of methylene chloride dehydrated by synthetic zeolite and 70 g of 1,4-dioxane were charged into the 1 liter glass reactor used in Example 1 and dissolved (specific gravity of this solution: 1.35). 79.5 g (0.497 mol) of bromine was added dropwise from the dropping funnel in 9 minutes while this solution was stirred and the mixture solvent was refluxed (addition rate of bromine: 1.09 mmol/sec based on 1 mol of the raw material). After the end of addition, the reaction solution was kept stirred for 30 minutes while the mixture solvent was refluxed to terminate the addition reaction of bromine.

The obtained reaction solution was then treated in the same manner as in Example 1 to obtain 203.3 g of a white solid product (yield: 96.8%). When the obtained product was analyzed by $^1$H-NMR and FT-IR as in Example 1, it was confirmed that the product was 2,2-bis{3,5-dibromo-4-(2,3-dibromo-2-methylpropyloxy)phenyl}propane. This bromine compound had a purity of 96.5% and a bromine content of 65.3% (theoretical value: 65.8%).

Example 3

Bromination was carried out in the same manner as in Example 2 except that 128.7 g (0.216 mol) of bis{(3,5-dibromo-4-allyloxy)phenyl}methane (specific gravity of the solution: 1.34) was used in place of 2,2-bis{(3,5-dibromo-4-isobutenyloxy)phenyl}propane and 79.5 g of bromine was added dropwise in 8.3 minutes instead of 9 minutes to obtain 191.4 g of a product (yield: 96.7%).

When the obtained product was analyzed by $^1$H-NMR and FT-IR as in Example 1, it was confirmed that the product was bis{3,5-dibromo-4-(2,3-dibromopropyloxy)phenyl}methane. This bromine compound had a purity of 96.7% and a bromine content of 69.5% (theoretical value: 69.8%).

Example 4

Bromination was carried out in the same manner as in Example 1 except that 134.8 g (0.216 mol) of bis{(3,5-dibromo-4-isobutenyloxy)phenyl}methane was used in place of 135 g of 2,2-bis{(3,5-dibromo-4-allyloxy)phenyl}propane (specific gravity of the solution: 1.47) to obtain 197.6 g of a product (yield: 96.9%).

When the obtained product was analyzed by $^1$H-NMR and FT-IR as in Example 1, it was confirmed that the product was bis{3,5-dibromo-4-(2,3-dibromo-2-methylpropyloxy)phenyl}methane. This bromine compound had a purity of 96.8% and a bromine content of 67.7% (theoretical value: 67.8%).

Example 5

Bromination was carried out in the same manner as in Example 1 except that 125.7 g (0.216 mol) of (3,3',5,5'-tetrabromo-4,4'-diallyloxy)biphenyl was used in place of 135 g of 2,2-bis{(3,5-dibromo-4-allyloxy)phenyl}propane (specific gravity of the solution: 1.47) to obtain 186.6 g of a product (yield: 95.8%).

When the obtained product was analyzed by $^1$H-NMR and FT-IR as in Example 1, it was confirmed that the product was {3,3',5,5'-tetrabromo-4,4'-(2,3-dibromopropyloxy)}biphenyl. This bromine compound had a purity of 95.7% and a bromine content of 70.8% (theoretical value: 70.9%).

Example 6

Bromination was carried out in the same manner as in Example 1 except that the amount of methylene chloride was changed from 230 g to 86 g (specific gravity of the solution: 1.42) and the amount of bromine was changed from 72.7 g to 75 g (0.469 mol) to obtain 199.5 g of a product (yield: 97.7%).

When the obtained product was analyzed by $^1$H-NMR and FT-IR as in Example 1, it was confirmed that the product was 2,2-bis{3,5-dibromo-4-(2,3-dibromopropyloxy)phenyl}propane. This bromine compound had a purity of 96.7%.

Example 7

Bromination was carried out in the same manner as in Example 1 except that the amount of 2,2-bis{(3,5-dibromo-4-allyloxy)phenyl}propane was changed from 135 g to 268 g (0.430 mol), the amount of methylene chloride was changed from 230 g to 493 g (specific gravity of the solution: 1.42) and the amount of bromine was changed from 72.7 g to 80 g (0.500 mol) to obtain 392.8 g of a product (yield: 96.9%).

When the obtained product was analyzed by $^1$H-NMR and FT-IR as in Example 1, it was confirmed that the product was 2,2-bis{3,5-dibromo-4-(2,3-dibromopropyloxy)phenyl}propane. This bromine compound had a purity of 96.8%.

Example 8

Bromination was carried out in the same manner as in Example 1 except that the amount of 2,2-bis{(3,5-dibromo-4-allyloxy)phenyl}propane was changed from 135 g to 162 g (0.260 mol), the amount of methylene chloride was changed from 230 g to 234 g (specific gravity of the solution: 1.47) and the amount of bromine was changed from 72.7 g to 95 g (0.594 mol) to obtain 234.7 g of a product (yield: 95.8%).

When the obtained product was analyzed by $^1$H-NMR and FT-IR as in Example 1, it was confirmed that the product was 2,2-bis{3,5-dibromo-4-(2,3-dibromopropyloxy)phenyl}propane. This bromine compound had a purity of 96.6%.

Example 9

Bromination was carried out in the same manner as in Example 1 except that 148 g (0.220 mol) of bis{3,5-dibromo-4-isobutenyloxy)phenyl}sulfone was used in place of 140.8 g of 2,2-bis{(3,5-dibromo-4-isobutenyloxy)phenyl}propane, the amount of methylene chloride was changed from 230 g to 121 g (specific gravity of the solution: 1.41) and the amount of bromine was changed from 72.7 g to 72.0 g (0.451 mol) to obtain 206.9 g of a product (yield: 94.8%).

When the obtained product was analyzed by $^1$H-NMR and FT-IR as in Example 1, it was confirmed that the product was bis{3,5-dibromo-4-(2,3-dibromo-2-methylpropyloxy)}sulfone. This bromine compound had a purity of 95.3% and a bromine content of 64.1% (theoretical value: 64.4%).

Comparative Example 1

The procedure of Example 1 was repeated except that bromine was added dropwise in 120 minutes and a bromination reaction was carried out without refluxing methylene chloride at a reaction temperature of 20° C. under cooling (addition rate of bromine based on 1 mol of the raw material: 0.29 mmol/sec). The yield of the obtained 2,2-bis{3,5-dibromo-4-(2,3-dibromopropyloxy)phenyl}propane was 96.5% but the purity thereof was low at 89.7%.

Comparative Example 2

The procedure of Example 1 was repeated except that bromine was added dropwise in 120 minutes to carry out a bromination reaction (addition rate of bromine based on 1 mol of the raw material: 0.29 mmol/sec). Although the temperature of the solution at the beginning of the addition of bromine was 20° C., it was gradually increased by reaction heat along with the addition of bromine and reached 37° C. at the end of addition. The reactor was not cooled and the reflux of methylene chloride did not occur. The obtained 2,2-bis{3,5-dibromo-4-(2,3-dibromopropyloxy)phenyl}propane had a low purity of 63.0%.

The results of Examples 1 to 9 and Comparative Example 1 are shown in Table 1 and Table 2. The solvents (A) and (B) had the following compositions.
(A) methylene chloride
(B) methylene chloride/1,4-dioxane=70/30 (weight ratio)

The addition rate was the addition rate of bromine based on 1 mol of the raw material.

TABLE 1

|  | Ex. 1 | Ex. 2 | Ex. 3 | Ex. 4 | Ex. 5 |
|---|---|---|---|---|---|
| raw material compound (raw material No.) | (1) | (2) | (3) | (4) | (5) |
| amount of raw material (mol) | 0.216 | 0.216 | 0.216 | 0.216 | 0.216 |
| solvent | (A) | (B) | (B) | (A) | (A) |
| concentration of raw material (mol/L) | 0.87 | 0.78 | 0.80 | 0.87 | 0.89 |
| amount of bromine (mol) | 0.455 | 0.497 | 0.497 | 0.455 | 0.455 |
| addition rate (mmol/sec) | 4.4 | 4.3 | 4.6 | 4.4 | 4.4 |
| concentration of raw material × addition rate | 3.8 | 3.3 | 3.7 | 3.8 | 3.9 |
| ratio of solvent/raw material compound (molecules/unsaturated group) | 6.25 | 6.3 | 6.3 | 6.25 | 6.25 |
| Yield (%) | 97.2 | 96.8 | 96.7 | 96.9 | 95.8 |
| Purity (%) | 96.8 | 96.5 | 96.7 | 96.8 | 95.7 |

Ex. = Example

TABLE 2

|  | Ex. 6 | Ex. 7 | Ex. 8 | Ex. 9 | C. Ex. 1 |
|---|---|---|---|---|---|
| raw material compound (raw material No.) | (1) | (1) | (1) | (6) | (1) |
| amount of raw material (mol) | 0.216 | 0.430 | 0.260 | 0.220 | 0.216 |
| solvent | (A) | (A) | (A) | (A) | (A) |
| concentration of raw material (mol/L) | 1.39 | 0.80 | 0.97 | 1.15 | 0.87 |
| amount of bromine (mol) | 0.469 | 0.500 | 0.594 | 0.451 | 0.455 |
| addition rate (mmol/sec) | 4.5 | 2.4 | 4.8 | 4.3 | 0.29 |
| concentration of raw material × addition rate | 6.3 | 1.9 | 4.6 | 4.9 | 0.25 |
| ratio of solvent/raw material compound (molecules/unsaturated group) | 2.35 | 6.75 | 5.3 | 3.25 | 6.25 |
| Yield (%) | 97.7 | 96.9 | 95.8 | 94.8 | 96.5 |
| Purity (%) | 96.7 | 96.8 | 96.6 | 95.3 | 89.7 |

Ex. = Example, C. Ex. = Comparative Example

Example 10

135 g (0.216 mol) of 2,2-bis{(3,5-dibromo-4-allyloxy)phenyl}propane and 230 g of methylene chloride dehydrated by synthetic zeolite were charged into a 1 liter glass reactor equipped with a stirrer, reflux condenser, thermometer and dropping funnel and dissolved. To this solution was added 0.36 g (0.0113 mol) of methanol (number of hydroxyl groups based on 100 aliphatic unsaturated groups: 2.6). This solution had a water content of 200 ppm (number of water molecules based on 100 aliphatic unsaturated groups: 0.94). Thereafter, this solution was cooled to about 2° C., and 72.7 g (0.455 mol) of bromine was added dropwise from the dropping funnel in 60 minutes under agitation. At the end of addition, the temperature of the reaction solution was 16° C. After the end of addition, the reaction solution was kept stirred for 30 minutes to terminate the addition reaction of bromine.

After excessive bromine contained in the reaction solution was reducted by 50 g of a 15 wt % aqueous solution of sodium bisulfite, generated hydrogen bromide was neutralized with a 25 wt % aqueous solution of sodium hydroxide. Thereafter, a methylene chloride layer was separated from this solution, and about 90% of methylene chloride was evaporated and thereafter, 500 ml of methanol was added to precipitate a reaction product, and the precipitate was filtered off to take out a bulk solid. This bulk solid was ground with a mortar, and the ground product was dried at a temperature of 80° C. and a reduced pressure of 5 mmHg for 3 hours to obtain 198.5 g of a product (yield: 97.0%).

When the obtained product was analyzed by $^1$H-NMR, a signal derived from —CHBr— was observed at 4.51 to 4.53 ppm and a signal derived from —CH$_2$Br was observed at 3.94 to 4.09 ppm. It was confirmed from FT-IR analysis that the absorption of —O—CH$_2$— was observed and the absorption of an allyl group was not observed. It was confirmed from the results of the above analyses that the product was mainly 2,2-bis{3,5-dibromo-4-(2,3-dibromopropyloxy)phenyl}propane. This bromine compound had a purity of 95.1% and contained 0.004 mol of impurities derived from water and 0.015 mol of impurities derived from methanol based on 1 mol of 2,2-bis{3,5-dibromo-4-(2,3-dibromopropyloxy)phenyl}propane. The inclination angle of the bromine compound was 44°.

Example 11

The procedure of Example 10 was repeated to obtain mainly 2,2-bis{3,5-dibromo-4-(2,3-dibromopropyloxy)phenyl}propane except that 0.36 g (0.00783 mol, number of hydroxyl groups based on 100 aliphatic unsaturated groups: 1.8) of ethanol was used in place of methanol. This bromine compound had a purity of 95.3% and contained 0.004 mol of impurities derived from water and 0.013 mol of impurities derived from ethanol based on 1 mol of 2,2-bis{3,5-dibromo-4-(2,3-dibromopropyloxy)phenyl}propane.

Example 12

The procedure of Example 10 was repeated except that 2.33 g (0.0388 mol, number of hydroxyl groups based on 100 aliphatic unsaturated groups: 9.0) of i-propanol was used in place of methanol and the initial temperature of the reaction solution was set to 25° C. At the end of the addition of bromine, the temperature of the reaction solution was 360° C. After the end of addition, the reaction solution was kept stirred for 30 minutes to terminate the addition reaction of bromine and treated in the same manner as in Example 1 to obtain mainly 2,2-bis{3,5-dibromo-4-(2,3-dibromopropyloxy)phenyl}propane. This bromine compound had a purity of 95.0% and contained 0.003 mol of impurities derived from water and 0.037 mol of impurities derived from i-propanol based on 1 mol of 2,2-bis{3,5-dibromo-4-(2,3-dibromopropyloxy)phenyl}propane.

Example 13

The procedure of Example 12 was repeated to obtain mainly 2,2-bis{3,5-dibromo-4-(2,3-dibromopropyloxy)phenyl}propane except that 1.13 g (0.015 mol, number of hydroxyl groups based on 100 aliphatic unsaturated groups: 3.5) of n-butanol was used in place of i-propanol. This bromine compound had a purity of 94.9% and contained 0.003 mol of impurities derived from water and 0.021 mol of impurities derived from n-butanol based on 1 mol of 2,2-bis{3,5-dibromo-4-(2,3-dibromopropyloxy)phenyl}propane.

Example 14

135 g (0.216 mol) of 2,2-bis{(3,5-dibromo-4-allyloxy)phenyl}propane and 230 g of methylene chloride were charged into the glass reactor used in Example 10 and dissolved. To this solution was added 0.72 g (0.0157 mol) of ethanol (number of hydroxyl groups based on 100 aliphatic unsaturated groups: 3.6). The water content of this solution was 500 ppm (number of water molecules based on 100 aliphatic unsaturated groups: 2.4). Thereafter, this solution was cooled to about 2° C., and 72.7 g (0.455 mol) of bromine was added dropwise from the dropping funnel in 60 minutes under agitation. At the end of addition, the temperature of the reaction solution was 16° C. After the end of addition, the reaction solution was kept stirred for 30 minutes to terminate the addition reaction of bromine.

This reaction solution was then treated in the same manner as in Example 10 to obtain mainly 2,2-bis{3,5-dibromo-4-(2,3-dibromopropyloxy)phenyl}propane. This bromine compound had a purity of 94.9% and contained 0.005 mol of impurities derived from water and 0.016 mol of impurities derived from ethanol based on 1 mol of 2,2-bis{3,5-dibromo-4-(2,3-dibromopropyloxy)phenyl}propane. The inclination angle of the bromine compound was 45°.

Example 15

The procedure of Example 10 was repeated to obtain mainly 2,2-bis{3,5-dibromo-4-(2,3-dibromopropyloxy)phenyl}propane except that the addition time of bromine was set to 120 minutes, the reaction solution was kept stirred for 30 minutes after the end of addition, and the temperature of the reaction solution was kept at 20° C. by cooling during a bromination reaction. This bromine compound had a purity of 95.2% and contained 0.003 mol of impurities derived from water and 0.015 mol of impurities derived from methanol based on 1 mol of 2,2-bis{3,5-dibromo-4-(2,3-dibromopropyloxy)phenyl}propane.

Example 16

0.72 g (0.016 mol, number of hydroxyl groups based on 100 aliphatic unsaturated groups: 3.6) of ethanol was used in place of methanol in Example 10, the amount of methylene chloride was changed from 230 g to 615 g (water content of this solution: 200 ppm, number of water molecules based on 100 aliphatic unsaturated groups: 1.9), the reaction temperature was set to 39 to 41° C., and 80.0 g (0.501 mol) of bromine was added dropwise in about 5 minutes while the solvent was refluxed. After the end of the addition of bromine, the reaction solution was kept stirred for 60 minutes to terminate the addition reaction of bromine.

This reaction solution was then treated in the same manner as in Example 10 to obtain mainly 2,2-bis{3,5-dibromo-4-(2,3-dibromopropyloxy)phenyl}propane. This bromine compound had a purity of 96.1% and contained 0.003 mol of impurities derived from water and 0.016 mol of impurities derived from methanol based on 1 mol of 2,2-bis{3,5-dibromo-4-(2,3-dibromopropyloxy)phenyl}propane. The inclination angle of the bromine compound was 41°.

Example 17

135 g (0.207 mol) of 2,2-bis{(3,5-dibromo-4-isobutenyloxy)phenyl}propane and 230 g of methylene chloride dehydrated by synthetic zeolite were charged into the glass reactor used in Example 10 and dissolved. To this solution was added 0.36 g (0.0113 mol) of methanol (number of hydroxyl groups based on 100 aliphatic unsaturated groups: 2.7). The water content of this solution was 200 ppm (number of water molecules based on 100 aliphatic unsaturated groups: 0.98) was 200 ppm. Thereafter, this solution was cooled to about 2° C., and 72.0 g (0.419 mol) of bromine was added dropwise from the dropping funnel in 60 minutes under agitation. At the end of addition, the temperature of the reaction solution was 16 C. After the end of addition, the reaction solution was kept stirred for 30 minutes to terminate the addition reaction of bromine.

This reaction solution was then treated in the same manner as in Example 10 to obtain mainly 2,2-bis{3,5-dibromo-4-(2,3-dibromo-2-methylpropyloxy)phenyl}propane. This bromine compound had a purity of 94.9% and contained 0.003 mol of impurities derived from water and 0.019 mol of impurities derived from methanol based on 1 mol of 2,2-bis{3,5-dibromo-4-(2,3-dibromo-2-methylpropyloxy)phenyl}propane.

Example 18

135 g (0.209 mol) of 2,2-bis{(3,5-dibromo-4-allyloxy)phenyl)sulfone and 230 g of methylene chloride were charged into the glass reactor used in Example 10 and dissolved. To this solution was added 1.54 g (0.0335 mol) of ethanol (number of hydroxyl groups based on 100 aliphatic unsaturated groups: 8.0). The water content of this solution was 500 ppm (number of water molecules based on 100 aliphatic unsaturated groups: 2.4). Thereafter, this solution was cooled to about 2° C., and 80.0 g (0.501 mol) of bromine was added dropwise from the dropping funnel in 60 minutes under agitation. At the end of addition, the temperature of the reaction solution was 16° C. After the end of addition, the reaction solution was kept stirred for 30 minutes to terminate the addition reaction of bromine.

This reaction solution was then treated in the same manner as in Example 10 to obtain mainly 2,2-bis{3,5-dibromo-4-(2,3-dibromopropyloxy)phenyl)sulfone. This bromine compound had a purity of 93.7% and contained 0.005 mol of impurities derived from water and 0.040 mol of impurities derived from ethanol based on 1 mol of 2,2-bis{3,5-dibromo-4-(2,3-dibromopropyloxy)phenyl}sulfone.

Example 19

135 g (0.227 mol) of bis{(3,5-dibromo-4-allyloxy)phenyl)methane and 230 g of chloroform dehydrated by synthetic zeolite were charged into the glass reactor used in Example 10 and dissolved. To this solution was added 2.33 g (0.0388 mol) of n-propanol (number of hydroxyl groups based on 100 aliphatic unsaturated groups: 8.5). The water content of this solution was 200 ppm (number of water molecules based on 100 aliphatic unsaturated groups: 0.90). Thereafter, the temperature of this solution was adjusted to 25° C., and 80.0 g (0.501 mol) of bromine was added dropwise from the dropping funnel in 100 minutes under agitation. At the end of addition, the temperature of the reaction solution was 35° C. After the end of addition, the reaction solution was kept stirred for 30 minutes to terminate the addition reaction of bromine.

This reaction solution was then treated in the same manner as in Example 10 to obtain mainly 2,2-bis{3,5-dibromo-4-(2,3-dibromopropyloxy)phenyl}methane. The bromine compound had a purity of 94.5% and contained 0.003 mol of impurities derived from water and 0.036 mol of impurities derived from n-propyl alcohol based on 1 mol of 2,2-bis{3,5-dibromo-4-(2,3-dibromopropyloxy)phenyl}methane.

Example 20

135 g (0.232 mol) of (3,3',5,5'-tetrabromo-4,4'-diallyloxy)biphenyl and 615 g of 1,4-dioxane dehydrated by synthetic zeolite were charged into the glass reactor used in Example 10 and dissolved. To this solution was added 1.54 g (0.0335 mol) of ethanol (number of hydroxyl groups based on 100 aliphatic unsaturated groups: 7.2). The water content of this solution was 400 ppm (number of water molecules based on 100 aliphatic unsaturated groups: 3.6). Thereafter, the temperature of this solution was adjusted to 25° C., and 80.0 g (0.501 mol) of bromine was added dropwise from the dropping funnel in 100 minutes under agitation. At the end of addition, the temperature of the reaction solution was 35° C. After the end of addition, the reaction solution was kept stirred for 30 minutes to terminate the addition reaction of bromine.

This reaction solution was then treated in the same manner as in Example 10 to obtain mainly {3,3',5,5'-tetrabromo-4,4'-(2,3-dibromopropyloxy)}biphenyl. The bromine compound had a purity of 94.0% and contained 0.005 mol of impurities derived from water and 0.032 mol of impurities derived from ethanol based on 1 mol of {3,3',5,5'-tetrabromo-4,4'-(2,3-dibromopropyloxy)}biphenyl.

The results of Examples 10 to 20 are shown in Table 3 and Table 4.

In Table 3 and Table 4, the concentration of a compound having a hydroxyl group indicates the number of hydroxyl groups based on 100 unsaturated groups of a compound having an aliphatic unsaturated bond, and the concentration of water indicates the number of water molecules based on 100 unsaturated groups of a compound having an aliphatic unsaturated bond. The amount (mols) of impurities derived from water and the amount (mols) of impurities derived from a compound having a hydroxyl group are based on 1 mol of the obtained bromine compound.

TABLE 3

|  | Ex. 10 | Ex. 11 | Ex. 12 | Ex. 13 | Ex. 14 | Ex. 15 |
| --- | --- | --- | --- | --- | --- | --- |
| raw material compound (raw material No.) | (1) | (1) | (1) | (1) | (1) | (1) |
| solvent | methylene chloride | methylene chloride | methylene chloride | methylene chloride | methylene chloride | methylene chloride |
| compound having hydroxyl group | methanol | ethanol | i-propanol | n-butanol | ethanol | methanol |
| concentration of compound having hydroxyl group | 2.6 | 1.8 | 9.0 | 3.5 | 3.6 | 2.6 |
| concentration of water | 0.94 | 0.94 | 0.94 | 0.94 | 2.4 | 0.94 |
| molar ratio of bromine/raw material compound | 2.1 | 2.1 | 2.1 | 2.1 | 2.1 | 2.1 |
| Addition time (min) | 60 | 60 | 60 | 60 | 60 | 120 |
| reaction temperature (° C.) | 2→16 | 2→16 | 25→36 | 25→36 | 25→36 | 20 |
| Purity (%) | 95.1 | 95.3 | 95.0 | 94.9 | 94.9 | 95.2 |
| impurities derived from water (mols) | 0.004 | 0.004 | 0.003 | 0.003 | 0.005 | 0.003 |
| impurities derived from compound having hydroxyl group (mols) | 0.015 | 0.013 | 0.037 | 0.021 | 0.016 | 0.015 |

TABLE 4

|  | Ex. 16 | Ex. 17 | Ex. 18 | Ex. 19 | Ex. 20 |
| --- | --- | --- | --- | --- | --- |
| raw material compound (raw material No.) | (1) | (2) | (7) | (3) | (5) |
| solvent | methylene chloride | methylene chloride | methylene chloride | chloroform | 1,4-dioxane |
| compound having hydroxyl group | ethanol | methanol | ethanol | n-propanol | ethanol |
| concentration of compound having hydroxyl group | 3.6 | 2.7 | 8.0 | 8.6 | 7.2 |
| concentration of water | 1.9 | 0.98 | 2.4 | 0.90 | 3.6 |
| molar ratio of bromine/raw material compound | 2.3 | 2.2 | 2.4 | 2.2 | 2.2 |
| Addition time (min) | 5 | 60 | 60 | 100 | 100 |
| reaction temperature (° C.) | 39~41 | 2→16 | 25→36 | 25→35 | 25→35 |
| Purity (%) | 96.1 | 94.9 | 93.7 | 94.5 | 94.0 |
| impurities derived from water (mols) | 0.003 | 0.003 | 0.005 | 0.003 | 0.005 |
| impurities derived from compound having hydroxyl group (mols) | 0.016 | 0.019 | 0.040 | 0.036 | 0.032 |

Example 21

72.6 g (0.454 mol) of bromine was charged into a 1 liter glass reactor equipped with a stirrer, reflux condenser, thermometer and dropping funnel. A solution was prepared by dissolving 135 g (0.216 mol) of 2,2-bis{(3,5-dibromo-4-allyloxy)phenyl}propane in 230 g of methylene chloride (water content of this solution; 200 ppm, number of water molecules based on 100 aliphatic unsaturated groups: 0.94). Thereafter, 365 g of the methylene chloride solution of 2,2-bis{(3,5-dibromo-4-allyloxy)phenyl}propane was added dropwise from the dropping funnel to bromine at a temperature of 15 to 20° C. in 60 minutes while the contents of the reactor were stirred. After the end of addition, the reaction solution was kept stirred at a temperature of 15 to 20° C. for 30 minutes to terminate the addition reaction of bromine.

After excessive bromine contained in the reaction solution was reduced by 100 g of a 15 wt % aqueous solution of sodium bisulfite, generated hydrogen bromide was neutralized with a 25 wt % aqueous solution of sodium hydroxide. Thereafter, a methylene chloride layer was separated from this solution, and about 90% of methylene chloride was evaporated and thereafter, 500 ml of methanol was added to precipitate a reaction product, and the precipitate was filtered off to take out a bulk solid. This bulk solid was ground with a mortar, and the ground product was dried at a temperature of 80° C. and a reduced pressure of 5 mmHg for 3 hours to obtain a product.

When the obtained product was analyzed by $^1$H-NMR, a signal derived from —CHBr— was observed at 4.51 to 4.53 ppm and a signal derived from —CH$_2$Br was observed at 3.94 to 4.09 ppm. It was confirmed from FT-IR analysis that the absorption of —O—CH$_2$— was observed and the absorption of an allyl group was not observed. It was confirmed from the results of the above analyses that the product was 2,2-bis{3,5-dibromo-4-(2,3-dibromopropyloxy)phenyl}propane. This bromine compound had a purity of 96.5% and a bromine content of 67.5% (theoretical value: 67.8%).

Example 22

72.6 g (0.454 mol) of bromine and 58.1 g of methylene chloride were charged into a 1 liter glass reactor equipped with a stirrer, reflux condenser, thermometer and dropping funnel. Thereafter, 135 g (0.216 mol) of 2,2-bis{(3,5-dibromo-4-allyloxy)phenyl}propane was added dropwise from the dropping funnel to the resulting bromine solution at a temperature of 15 to 20° C. in 60 minutes while the contents of the reactor were stirred. After the end of addition, the reaction solution was kept stirred at a temperature of 15 to 20° C. for 30 minutes to terminate the addition reaction of bromine.

The obtained reaction solution was then treated in the same manner as in Example 21 to obtain a white solid product. When the obtained product was analyzed by $^1$H-NMR and FT-IR as in Example 21, it was confirmed that the product was 2,2-bis{3,5-dibromo-4-(2,3-dibromopropyloxy)phenyl}propane. This bromine compound had a purity of 96.3% and a bromine content of 67.5% (theoretical value: 67.8%).

Example 23

72.6 g (0.454 mol) of bromine and 58.1 g of methylene chloride were charged into a 1 liter glass reactor equipped with a stirrer, reflux condenser, thermometer and dropping funnel. A solution was prepared by dissolving 140.8 g (0.216 mol) of 2,2-bis{(3,5-dibromo-4-isobutenyloxy)phenyl}propane in 230 g of methylene chloride. Thereafter, 370.8 g of the methylene chloride solution of 2,2-bis{(3,5-dibromo-4-isobutenyloxy)phenyl}propane was added dropwise from the dropping funnel to the resulting bromine solution at a temperature of 15 to 20° C. in 120 minutes while the contents of the reactor were stirred. After the end of addition, the reaction solution was kept stirred at a temperature of 15 to 20° C. for 30 minutes to terminate the addition reaction of bromine.

The obtained reaction solution was then treated in the same manner as in Example 21 to obtain a white solid product. When the obtained product was analyzed by $^1$H-NMR and FT-IR as in Example 21, it was confirmed that the product was 2,2-bis{3,5-dibromo-4-(2,3-dibromo-2-methylpropyloxy)phenyl}propane. This bromine compound had a purity of 96.5% and a bromine content of 65.3% (theoretical value: 65.8%).

Example 24

72.6 g (0.454 mol) of bromine and 58.1 g of methylene chloride were charged into a 1 liter glass reactor equipped with a stirrer, reflux condenser, thermometer and dropping funnel. A solution was prepared by dissolving 128.7 g (0.216 mol) of bis{(3,5-dibromo-4-allyloxy)phenyl}methane in a mixture solvent of 161 g of methylene chloride and 69 g of 1,4-dioxane. Thereafter, 358.7 g of the solution of bis{(3,5-dibromo-4-allyloxy)phenyl}methane was added dropwise from the dropping funnel to the resulting bromine solution at a temperature of 15 to 20° C. in 60 minutes while the contents of the reactor were stirred. After the end of addition, the reaction solution was kept stirred at a temperature of 15 to 20° C. for 30 minutes to terminate the addition reaction of bromine.

The obtained reaction solution was then treated in the same manner as in Example 21 to obtain a white solid product. When the obtained product was analyzed by $^1$H-NMR and FT-IR as in Example 21, it was confirmed that the product was bis{3,5-dibromo-4-(2,3-dibromopropyloxy)phenyl}methane. This bromine compound had a purity of 96.0% and a bromine content of 69.5% (theoretical value: 69.8%).

Example 25

7.26 g (0.045 mol) of bromine and 217.7 g of methylene chloride were charged into a 1 liter glass reactor equipped with a stirrer, reflux condenser, thermometer and dropping funnel. A solution was prepared by dissolving 13.5 g (0.0216 mol) of bis{(3,5-dibromo-4-isobutenyloxy)phenyl}methane in 23 g of methylene chloride. Thereafter, 36.5 g of the methylene chloride solution of bis{(3,5-dibromo-4-isobutenyloxy)phenyl}methane was added dropwise from the dropping funnel to the resulting bromine solution at a temperature of 15 to 20° C. in 60 minutes while the contents of the reactor were stirred. After the end of addition, the reaction solution was kept stirred at a temperature of 15 to 20° C. for 30 minutes to terminate the addition reaction of bromine.

The obtained reaction solution was then treated in the same manner as in Example 21 to obtain a white solid product. When the obtained product was analyzed by $^1$H-NMR and FT-IR as in Example 21, it was confirmed that the product was bis(3,5-dibromo-4-(2,3-dibromo-2-methylpropyloxy)phenyl)methane. This bromine compound had a purity of 96.2% and a bromine content of 67.7% (theoretical value: 67.8%).

Example 26

72.6 g (0.454 mol) of bromine and 300 g of methylene chloride were charged into a 1 liter glass reactor equipped with a stirrer, reflux condenser, thermometer and dropping funnel. A solution was prepared by dissolving 125.7 g (0.216 mol) of (3,3',5,5'-tetrabromo-4,4'-diallyloxy)biphenyl in 230 g of methylene chloride. Thereafter, 355.7 g of the methylene chloride solution of (3,3',5,5'-tetrabromo-4,4'-diallyloxy)biphenyl was added dropwise from the dropping funnel to the resulting bromine solution at a temperature of 15 to 20° C. in 60 minutes while the contents of the reactor were stirred. After the end of addition, the reaction solution was kept stirred at a temperature of 15 to 20° C. for 30 minutes to terminate the addition reaction of bromine.

The obtained reaction solution was then treated in the same manner as in Example 21 to obtain a white solid product. When the obtained product was analyzed by $^1$H-NMR and FT-IR as in Example 21, it was confirmed that the product was {3,3',5,5'-tetrabromo-4,4'-(2,3-dibromopropyloxy)}biphenyl. This bromine compound had a purity of 95.7% and a bromine content of 70.7% (theoretical value: 70.9%).

Example 27

72.6 g (0.454 mol) of bromine and 14.5 g of methylene chloride were charged into a 1 liter glass reactor equipped with a stirrer, reflux condenser, thermometer and dropping funnel. A solution was prepared by dissolving 139.5 g (0.216 mol) of bis{(3,5-dibromo-4-allyloxy)phenyl}sulfone in 230 g of methylene chloride. Thereafter, 369.5 g of the methylene chloride solution of bis{(3,5-dibromo-4-allyloxy)phenyl} sulfone was added dropwise from the dropping funnel to the resulting bromine solution at a temperature of 15 to 20° C. in 60 minutes while the contents of the reactor were stirred. After the end of addition, the reaction solution was kept stirred at a temperature of 15 to 20° C. for 30 minutes to terminate the addition reaction of bromine.

The obtained reaction solution was then treated in the same manner as in Example 21 to obtain a white solid product. When the obtained product was analyzed by $^1$H-NMR and FT-IR as in Example 21, it was confirmed that the product was bis{3,5-dibromo-4-(2,3-dibromopropyloxy)phenyl}sulfone. This bromine compound had a purity of 95.4% and a bromine content of 66.0% (theoretical value: 66.2%).

Example 28

72.6 g (0.454 mol) of bromine and 58.1 g of methylene chloride were charged into a 1 liter glass reactor equipped with a stirrer, reflux condenser, thermometer and dropping funnel. A solution was prepared by dissolving 145.6 g (0.216 mol) of bis{(3,5-dibromo-4-isobutenyloxy)phenyl)sulfone in a mixture solvent of 161 g of methylene chloride and 69 g of 1,4-dioxane. Thereafter, 375.6 g of the methylene chloride solution of bis{(3,5-dibromo-4-isobutenyloxy) phenyl}sulfone was added dropwise from the dropping funnel to the resulting bromine solution at a temperature of 15 to 20° C. in 120 minutes while the contents of the reactor were stirred. After the end of addition, the reaction solution was kept stirred at a temperature of 15 to 20° C. for 30 minutes to terminate the addition reaction of bromine.

The obtained reaction solution was then treated in the same manner as in Example 21 to obtain a white solid product. When the obtained product was analyzed by $^1$H-NMR and FT-IR as in Example 21, it was confirmed that the product was bis{3,5-dibromo-4-(2,3-dibromo-2-methylpropyloxy)}sulfone. This bromine compound had a purity of 95.0% and a bromine content of 64.1% (theoretical value: 64.4%).

The results of Examples 21 to 28 are shown in Table and Table 6.

TABLE 5

|  | Ex. 21 | Ex. 22 | Ex. 23 | Ex. 24 | Ex. 25 |
| --- | --- | --- | --- | --- | --- |
| addition method | adding raw material compound solution dropwise to bromine | adding raw material compound solution dropwise to bromine solution | adding raw material compound solution dropwise to bromine solution | adding raw material compound solution dropwise to bromine solution | adding raw material compound solution dropwise to bromine solution |
| raw material compound (raw material No.) | (1) | (1) | (2) | (3) | (4) |
| solvent | methylene chloride | — | methylene chloride | methylene chloride/ 1,4-dioxane | methylene chloride |
| bromine, bromine solution | bromine | bromine | bromine | bromine | bromine |
| solvent | — | methylene chloride | methylene chloride | methylene chloride | methylene chloride |
| molar ratio of bromine/raw material compound | 2.1 | 2.1 | 2.1 | 2.1 | 2.1 |
| addition time (min) | 60 | 60 | 120 | 60 | 60 |
| reaction temperature (° C.) | 15~20 | 15~20 | 15~20 | 15~20 | 15~20 |
| purity (%) | 96.5 | 96.3 | 96.5 | 96.0 | 96.2 |

TABLE 6

|  | Ex. 26 | Ex. 27 | Ex. 28 |
|---|---|---|---|
| addition method | adding raw material compound solution dropwise to bromine solution | adding raw material compound solution dropwise to bromine solution | adding raw material compound solution dropwise to bromine solution |
| raw material compound (raw material No.) | (5) | (7) | (6) |
| solvent | methylene chloride | methylene chloride | methylene chloride/ 1,4-dioxane |
| bromine, bromine solution | bromine | bromine | bromine |
| solvent | methylene chloride | methylene chloride | methylene chloride |
| molar ratio of bromine/raw material compound | 2.1 | 2.1 | 2.1 |
| addition time (min) | 60 | 60 | 120 |
| reaction temperature (° C.) | 15~20 | 15~20 | 15~20 |
| purity (%) | 95.7 | 95.4 | 95.0 |

Example 29

72.7 g (0.455 mol) of bromine was charged into a 500 mm liter glass reactor equipped with a stirrer, reflux condenser, thermometer and dropping funnel. A solution was prepared by dissolving 135 g (0.216 mol) of 2,2-bis{(3,5-dibromo-4-allyloxy)phenyl}propane in 230 g of methylene chloride dehydrated by synthetic zeolite and adding 0.36 g (0.0113 mol, number of hydroxyl groups based on 100 aliphatic unsaturated groups: 2.6) of methanol to the resulting solution. Thereafter, bromine in the reactor was cooled to 2° C., and the methylene chloride solution of 2,2-bis{(3,5-dibromo-4-allyloxy)phenyl}propane was added dropwise from the dropping funnel to bromine in 60 minutes under agitation. At the end of addition, the temperature of the reaction solution was 16° C. After the end of addition, the reaction solution was kept stirred for 30 minutes to terminate the addition reaction of bromine. The water content of the reaction solution was 200 ppm (number of water molecules based on 100 aliphatic unsaturated groups: 1.1).

After excessive bromine contained in the reaction solution was reduced with 50 g of a 15 wt % aqueous solution of sodium bisulfite, generated hydrogen bromide was neutralized with a 25 wt % aqueous solution of sodium hydroxide. Thereafter, 100 g of ion exchange water was added, a methylene chloride layer was separated from this solution after agitation, and about 90% of methylene chloride was evaporated and therafter, 500 ml of methanol was added to precipitate a reaction product, and the precipitate was filtered off to take out a bulk solid. This bulk solid was ground with a mortar and dried at a temperature of 80° C. and a reduced pressure of 5 mmHg for 3 hours to obtain a product.

When the obtained product was analyzed by $^1$H-NMR, a signal derived from —CHBr— was observed at 4.51 to 4.53 ppm and a signal derived from —CH$_2$Br was observed at 3.94 to 4.09 ppm. It was confirmed from FT-IR analysis that the absorption of —O—CH$_2$— was observed and the absorption of an allyl group was not observed. It was confirmed from the results of the above analyses that the product was mainly 2,2-bis{3,5-dibromo-4-(2,3-dibromopropyloxy)phenyl}propane. This bromine compound had a purity of 96.7% and contained 0.0023 mol of impurities derived from water and 0.0155 mol of impurities derived from methanol based on 1 mol of 2,2-bis{3,5-dibromo-4-(2,3-dibromopropyloxy)phenyl}propane. The inclination angle of the bromine compound was 40°.

Example 30

The procedure of Example 29 was repeated to carry out the addition reaction of bromine except that 0.36 g (0.00783 mol, number of hydroxyl groups based on 100 aliphatic unsaturated groups: 1.8) of ethanol was used in place of methanol. The water content of the reaction solution was 210 ppm (number of water molecules based on 100 aliphatic unsaturated groups: 1.2).

This reaction solution was then treated in the same manner as in Example 29 to obtain mainly 2,2-bis{3,5-dibromo-4-(2,3-dibromopropyloxy)phenyl}propane. This bromine compound had a purity of 96.1% and contained 0.0025 mol of impurities derived from water and 0.0124 mol of impurities derived from ethanol based on 1 mol of 2,2-bis{3,5-dibromo-4-(2,3-dibromopropyloxy)phenyl}propane. The inclination angle of the bromine compound was 4°.

Example 31

72.6 g (0.454 mol) of bromine and 230 g of methylene chloride were charged into a 1 liter glass reactor equipped with a stirrer, reflux condenser, thermometer and dropping funnel. A solution was prepared by dissolving 135 g (0.216 mol) of 2,2-bis{(3,5-dibromo-4-allyloxy)phenyl}propane in 230 g of methylene chloride and adding 0.36 g (0.00783 mol, number of hydroxyl groups based on 100 aliphatic unsaturated groups: 1.8) of ethanol to the resulting solution. Thereafter, the bromine solution in the reactor was cooled to 2° C., and the methylene chloride solution of 2,2-bis{(3,5-dibromo-4-allyloxy)phenyl}propane was added dropwise from the dropping funnel to the bromine solution in 60 minutes under agitation. At the end of addition, the temperature of the reaction solution was 16° C. After the end of addition, the reaction solution was kept stirred for 30 minutes to terminate the addition reaction of bromine. The water content of the reaction solution was 420 ppm (number of water molecules based on 100 aliphatic unsaturated groups: 3.6).

The obtained reaction solution was then treated in the same manner as in Example 29 to obtain a white solid product. When the obtained product was analyzed by $^1$H-NMR and FT-IR as in Example 29, it was confirmed that the product was mainly 2,2-bis{3,5-dibromo-4-(2,3-dibromopropyloxy)phenyl}propane. This bromine compound had a purity of 95.9% and contained 0.0041 mol of impurities derived from water and 0.0124 mol of impurities derived from ethanol based on 1 mol of 2,2-bis(3,5-dibromo-4-(2,3-dibromopropyloxy)phenyl}propane. The inclination angle of the bromine compound was 44°.

Example 32

72.6 g (0.454 mol) of bromine and 230 g of methylene chloride were charged into a 1 liter glass reactor equipped with a stirrer, reflux condenser, thermometer and dropping funnel. A solution was prepared by dissolving 135 g (0.216 mol) of 2,2-bis{(3,5-dibromo-4-allyloxy)phenyl}propane in 230 g of methylene chloride and adding 0.36 g (0.00783 mol, number of hydroxyl groups based on 100 aliphatic unsaturated groups: 1.8) of ethanol to the resulting solution. Thereafter, the methylene chloride solution of 2,2-bis{(3,5-dibromo-4-allyloxy)phenyl}propane was added dropwise from the dropping funnel to the bromine solution in 10 minutes while the contents of the reactor were stirred and methylene chloride was refluxed at a temperature of 39 to 41° C. After the end of addition, the reaction solution was kept stirred for 30 minutes while methylene chloride was refluxed at a temperature of 39 to 41° C. to terminate the addition reaction of bromine. The water content of the reaction solution was 420 ppm (number of water molecules based on 100 aliphatic unsaturated groups: 3.6).

The obtained reaction solution was then treated in the same manner as in Example 29 to obtain a white solid product. When the obtained product was analyzed by $^1$H-NMR and FT-IR as in Example 29, it was confirmed that the product was mainly 2,2-bis{3,5-dibromo-4-(2,3-dibromopropyloxy)phenyl}propane. This bromine compound had a purity of 96.4% and contained 0.0023 mol of impurities derived from water and 0.0123 mol of impurities derived from ethanol based on 1 mol of 2,2-bis(3,5-dibromo-4-(2,3-dibromopropyloxy)phenyl}propane.

Example 33

72.6 g (0.454 mol) of bromine, 230 g of methylene chloride dehydrated by synthetic zeolite and 0.36 g (0.00783 mol, number of hydroxyl groups based on 100 aliphatic unsaturated groups: 1.8) of ethanol were charged into a 500 ml glass reactor equipped with a stirrer, reflux condenser, thermometer and dropping funnel. 135 g (0.216 mol) of 2,2-bis{(3,5-dibromo-4-allyloxy)phenyl}propane was added to the bromine solution in 5 minutes while the contents of the reactor were stirred and methylene chloride was refluxed at a temperature of 39 to 41° C. After the end of addition, the reaction solution was kept stirred for 30 minutes while methylene chloride was refluxed at a temperature of 39 to 41° C. to terminate the addition reaction of bromine. The water content of the reaction solution was 210 ppm (number of water molecules based on 100 aliphatic unsaturated groups: 1.2).

The obtained reaction solution was then treated in the same manner as in Example 29 to obtain a white solid product. When the obtained product was analyzed by $^1$H-NMR and FT-IR as in Example 29, it was confirmed that the product was mainly 2,2-bis{3,5-dibromo-4-(2,3-dibromopropyloxy)phenyl}propane. This bromine compound had a purity of 96.5% and contained 0.0021 mol of impurities derived from water and 0.0135 mol of impurities derived from ethanol based on 1 mol of 2,2-bis{3,5-dibromo-4-(2,3-dibromopropyloxy)phenyl}propane.

Example 34

72.7 g (0.455 mol) of bromine was charged into a 1 liter glass reactor equipped with a stirrer, reflux condenser, thermometer and dropping funnel. A solution was prepared by dissolving 135 g (0.216 mol) of 2,2-bis{(3,5-dibromo-4-allyloxy)phenyl}propane in 230 g of methylene chloride dehydrated by synthetic zeolite and adding 0.36 g (0.0060 mol, number of hydroxyl groups based on 100 aliphatic unsaturated groups: 1.4) of i-propanol to the resulting solution. Thereafter, bromine contained in the reactor was cooled to about 2° C., and the solution of 2,2-bis{(3,5-dibromo-4-allyloxy)phenyl}propane was added dropwise from the dropping funnel to bromine in 60 minutes under agitation. At the end of addition, the temperature of the reaction solution was 20° C. After the end of addition, the reaction solution was kept stirred for 30 minutes to terminate the addition reaction of bromine. The water content of the reaction solution was 200 ppm (number of water molecules based on 100 aliphatic unsaturated groups: 1.1).

The obtained reaction solution was treated in the same manner as in Example 29 to obtain a white solid product. When the obtained product was analyzed by $^1$H-NMR and FT-IR as in Example 29, it was confirmed that the product was mainly 2,2-bis{3,5-dibromo-4-(2,3-dibromopropyloxy)phenyl}propane. This bromine compound had a purity of 96.3% and contained 0.0019 mol of impurities derived from water and 0.0146 mol of impurities derived from i-propanol based on 1 mol of 2,2-bis(3,5-dibromo-4-(2,3-dibromopropyloxy)phenyl}propane.

Example 35

72.7 g (0.455 mol) of bromine was charged into a 1 liter glass reactor equipped with a stirrer, reflux condenser, thermometer and dropping funnel. A solution was prepared by dissolving 135 g (0.216 mol) of 2,2-bis{(3,5-dibromo-4-allyloxy)phenyl}propane in 615 g of chloroform dehydrated by synthetic zeolite and adding 0.54 g (0.0169 mol, number of hydroxyl groups based on 100 aliphatic unsaturated groups: 3.9) of methanol to the resulting solution. Thereafter, bromine contained in the reactor was cooled to 2° C., and the chloroform solution of 2,2-bis{(3,5-dibromo-4-allyloxy)phenyl}propane was added dropwise from dropping funnel to bromine in 60 minutes under agitation. At the end of addition, the temperature of the reaction solution was 16° C. After the end of addition, the reaction solution was kept stirred for 30 minutes to terminate the addition reaction of bromine. The water content of the reaction solution was 100 ppm (number of water molecules based on 100 aliphatic unsaturated groups: 1.1).

After excessive bromine contained in the reaction solution was reducted by 50 g of a 15 wt % aqueous solution of sodium bisulfite, generated hydrogen bromide was neutralized with a 25 wt % aqueous solution of sodium hydroxide. Thereafter, 200 g of ion exchange water was added, a chloroform layer was separated from this solution after agitation, and about 90% of chloroform was evaporated and thereafter, 500 ml of methanol was added to precipitate a reaction product, and the precipitate was filtered off to take out a bulk solid. This bulk solid was ground with a mortar, and the ground product was dried at a temperature of 80° C. and a reduced pressure of 5 mmHg for 3 hours to obtain a product. When the obtained product was analyzed by $^1$H-NMR and FT-IR as in Example 29, it was confirmed that the product was mainly 2,2-bis{3,5-dibromo-4-(2,3-dibromopropyloxy)phenyl}propane. This bromine compound had a purity of 95.8% and contained 0.0022 mol of impurities derived from water and 0.0155 mol of impurities derived from methanol based on 1 mol of 2,2-bis{3,5-dibromo-4-(2,3-dibromopropyloxy)phenyl}propane.

Example 36

69.5 g (0.435 mol) of bromine was charged into a 500 ml glass reactor equipped with a stirrer, reflux condenser, thermometer and dropping funnel. A solution was prepared by dissolving 135 g (0.207 mol) of 2,2-bis{(3,5-dibromo-4-isobutenyloxy)phenyl}propane in 230 g of methylene chloride dehydrated by synthetic zeolite and adding 0.36 g (0.0113 mol, number of hydroxyl groups based on 100 aliphatic unsaturated groups: 2.7) of methanol to the resulting solution. Thereafter, bromine contained in the reactor was cooled to about 2° C., and the solution of 2,2-bis{(3, 5-dibromo-4-isobutenyloxy)phenyl}propane was added dropwise from the dropping funnel to bromine in 60 minutes under agitation. At the end of addition, the temperature of the reaction solution was 16° C. After the end of addition, the reaction solution was kept stirred for 30 minutes to terminate the addition reaction of bromine. The water content of the reaction solution was 190 ppm (number of water molecules based on 100 aliphatic unsaturated groups: 1.1).

The obtained reaction solution was then treated in the same manner as in Example 29 to obtain a white solid product. When the obtained product was analyzed by $^1$H-NMR and FT-IR as in Example 29, it was confirmed that the product was mainly 2,2-bis{3,5-dibromo-4-(2,3-dibromo-2-methylpropyloxy)phenyl}propane. This bromine compound had a purity of 95.8% and contained 0.0021 mol of impurities derived from water and 0.0212 mol of impurities derived from methanol based on 1 mol of 2,2-bis{3,5-dibromo-4-(2,3-dibromo-2-methylpropyloxy)phenyl}propane.

Example 37

70.1 g (0.439 mol) of bromine was charged into a 500 ml glass reactor equipped with a stirrer, reflux condenser, thermometer and dropping funnel. A solution was prepared by dissolving 135 g (0.209 mol) of bis{(3,5-dibromo-4-allyloxy)phenyl}sulfone in 230 g of methylene chloride dehydrated by synthetic zeolite and adding 0.36 g (0.0113 mol, number of hydroxyl groups based on 100 aliphatic unsaturated groups: 2.7) of methanol to the resulting solution. Thereafter, bromine contained in the reactor was cooled to about 2° C., and the solution of bis}(3,5-dibromo-4-allyloxy)phenyl}sulfone was added dropwise from the dropping funnel to bromine in 60 minutes under agitation. At the end of addition, the temperature of the reaction solution was 16° C. After the end of addition, the reaction solution was kept stirred for 30 minutes to terminate the addition reaction of bromine. The water content of the reaction solution was 180 ppm (number of water molecules based on 100 aliphatic unsaturated groups: 1.0).

The obtained reaction solution was then treated in the same manner as in Example 29 to obtain a white solid product. When the obtained product was analyzed by $^1$H-NMR and FT-IR as in Example 29, it was confirmed that the product was mainly bis(3,5-dibromo-4-(2,3-dibromopropyloxy)phenyl)sulfone. This bromine compound had a purity of 94.2% and contained 0.0020 mol of impurities derived from water and 0.0328 mol of impurities derived from methanol based on 1 mol of bis(3,5-dibromo-4-(2,3-dibromopropyloxy)phenyl}sulfone.

Example 38

76.2 g (0.477 mol) of bromine was charged into a 500 ml glass reactor equipped with a stirrer, reflux condenser, thermometer and dropping funnel. A solution was prepared by dissolving 135 g (0.227 mol) of bis{3,5-dibromo-4-allyloxy)phenyl}methane in 615 g of chloroform dehydrated by synthetic zeolite and adding 1.13 g (0.0157 mol, number of hydroxyl groups based on 100 aliphatic unsaturated groups: 3.5) of n-butanol to the resulting solution. Thereafter, bromine contained in the reactor was cooled to about 2° C., and the solution of bis(3,5-dibromo-4-allyloxy)phenyl}methane was added dropwise from the dropping funnel to bromine in 60 minutes under agitation. At the end of addition, the temperature of the reaction solution was 16° C. After the end of addition, the reaction solution was kept stirred for 30 minutes to terminate the addition reaction of bromine. The water content of the reaction solution was 100 ppm (number of water molecules based on 100 aliphatic unsaturated groups: 1.0).

The obtained reaction solution was then treated in the same manner as in Example 35 to obtain a white solid product. When the obtained product was analyzed by $^1$H-NMR and FT-IR as in Example 29, it was confirmed that the product was mainly bis{3,5-dibromo-4-(2,3-dibromopropyloxy)phenyl}methane. This bromine compound had a purity of 94.9% and contained 0.0014 mol of impurities derived from water and 0.0353 mol of impurities derived from n-butanol based on 1 mol of bis(3,5-dibromo-4-(2,3-dibromopropyloxy)phenyl}methane.

Example 39

77.9 g (0.487 mol) of bromine and 123 g of 1,4-dioxane dehydrated by synthetic zeolite were charged into a 1 liter glass reactor equipped with a stirrer, reflux condenser, thermometer and dropping funnel. A solution was prepared by dissolving 135 g (0.232 mol) of (3,3',5,5'-tetrabromo-4,4'-diallyloxy)biphenyl in 615 g of 1,4-dioxane dehydrated by synthetic zeolite and adding 1.13 g (0.0157 mol, number of hydroxyl groups based on 100 aliphatic unsaturated groups: 3.4) of n-butanol to the resulting solution. Thereafter, the temperature of the bromine solution contained in the reactor was adjusted to about 22° C., and the solution of (3,3',5,5'-tetrabromo-4,4'-diallyloxy)biphenyl was added dropwise from the dropping funnel to the bromine solution in 10 minutes under agitation. At the end of addition, the temperature of the reaction solution was 50° C. After the end of addition, the reaction solution was kept stirred for 30 minutes to terminate the addition reaction of bromine. The water content of the reaction solution was 120 ppm (number of water molecules based on 100 aliphatic unsaturated groups: 1.4).

After excessive bromine contained in the reaction solution was reduced with 50 g of a 15 wt % aqueous solution of sodium bisulfite, generated hydrogen bromide was neutralized with a 25 wt % aqueous solution of sodium hydroxide. Thereafter, 100 g of ion exchange water was added, a 1,4-dioxane layer was separated from this solution after agitation, and about 90% of 1,4-dioxane was evaporated and removed from the 1,4-dioxane layer. 500 ml of methanol was added to precipitate a reaction product, and the precipitate was filtered off to take out a bulk solid. This bulk solid was ground with a mortar and dried at a temperature of 80° C. and a reduced pressure of 5 mmHg for 3 hours to obtain a product.

When the obtained product was analyzed by $^1$H-NMR and FT-IR as in Example 29, it was confirmed that the product was mainly {3,3',5,5'-tetrabromo-4,4'-(2,3-dibromopropyloxy)}biphenyl. This bromine compound had a purity of 94.6% and contained 0.0018 mol of impurities derived from water and 0.0254 mol of impurities derived from n-butanol based on 1 mol of {3,3',5,5'-tetrabromo-4,4'-(2,3-dibromo-propyloxy)}biphenyl.

The results of Examples 29 to 39 are shown in Table 7 and Table 8.

In Table 7 and Table 8, the concentration of a compound having a hydroxyl group indicates the number of hydroxyl groups based on 100 unsaturated groups of a compound having an aliphatic unsaturated bond, and the concentration of water indicates the number of water molecules based on 100 unsaturated groups of a compound having an aliphatic unsaturated bond. The amount (mols) of impurities derived from water and the amount (mols) of impurities derived from a compound having a hydroxyl group are based on 1 mol of the obtained bromine compound.

TABLE 7

|  | Ex. 29 | Ex. 30 | Ex. 31 | Ex. 32 | Ex. 33 | Ex. 34 |
|---|---|---|---|---|---|---|
| addition method | adding raw material compound solution dropwise to bromine | adding raw material compound solution dropwise to bromine | adding raw material compound solution dropwise to bromine solution | adding raw material compound solution dropwise to bromine solution | adding raw material compound solution dropwise to bromine solution | adding raw material compound soluton dropwise to bromine |
| raw material compound (raw material No.) | (1) | (1) | (1) | (1) | (1) | (1) |
| solvent | methylene chloride | methylene chloride | methylene chloride | methylene chloride | — | methylene choride |
| bromine, bromine solution | bromine | bromine | bromine | bromine | bromine | bromine |
| solvent | — | — | methylene chloride | methylene chloride | methylene chloride | — |
| compound having hydroxyl group | methanol | ethanol | ethanol | ethanol | ethanol | 1-propanol |
| concentration of compound having hydroxyl group | 2.6 | 1.8 | 1.8 | 1.8 | 1.8 | 1.4 |
| concentration of water | 1.1 | 1.2 | 3.6 | 3.6 | 1.2 | 1.1 |
| molar ratio of bromine/ raw material compound | 2.1 | 2.1 | 2.1 | 2.1 | 2.1 | 2.1 |
| addition time (min) | 60 | 60 | 60 | 10 | 5 | 60 |
| reaction temperature (° C.) | 2~16 | 2~16 | 2~16 | 39~41 | 39~41 | 2~20 |
| Purity (%) | 96.7 | 96.1 | 95.9 | 96.4 | 96.5 | 96.3 |
| impurities derived from water (mols) | 0.0023 | 0.0025 | 0.0041 | 0.0023 | 0.0021 | 0.0019 |
| impurities derived from compound having hydroxyl group (mols) | 0.0155 | 0.0124 | 0.0124 | 0.0123 | 0.0135 | 0.0146 |

TABLE 8

|  | Ex. 35 | Ex. 36 | Ex. 37 | Ex. 38 | Ex. 39 |
|---|---|---|---|---|---|
| addition method | adding raw material compound solution dropwise to bromine | adding raw material compound solution dropwise to bromine | adding raw material compound solution dropwise to bromine | adding raw material compound solution dropwise to bromine | adding raw material compound solution dropwise to bromine solution |
| raw material compound (raw material No.) | (1) | (2) | (7) | (3) | (5) |
| solvent | chloroform | methylene chloride | methylene chloride | chloroform | 1,4-dioxane |
| bromine, bromine solution | bromine | bromine | bromine | bromine | bromine |
| solvent | — | — | — | — | 1,4-dioxane |
| compound having hydroxyl group | methanol | methanol | methanol | n-butanol | n-butanol |
| concentration of compound having hydroxyl group | 3.9 | 2.7 | 2.7 | 3.5 | 3.4 |
| concentration of water | 1.1 | 1.1 | 1.0 | 1.0 | 1.2 |
| molar ratio of bromine/ raw material compound | 2.1 | 2.1 | 2.1 | 2.1 | 2.1 |
| addition time (min) | 60 | 60 | 60 | 60 | 10 |
| reaction temperature (° C.) | 2~16 | 2~16 | 2~16 | 2~16 | 22~50 |
| Purity (%) | 95.8 | 95.8 | 94.2 | 94.9 | 94.6 |
| impurities derived from water (mols) | 0.0022 | 0.0021 | 0.0020 | 0.0014 | 0.0018 |
| impurities derived from compound having hydroxyl group (mols) | 0.0155 | 0.0212 | 0.0328 | 0.0353 | 0.0254 |

Example 40

1,000 g (1.60 mols) of 2,2-bis{(3,5-dibromo-4-allyloxy)phenyl}propane (raw material No. (1)) was dissolved in 1,703 g (20.0 mols) of methylene chloride. This solution had a specific gravity of 1.46 and contained 160 ppm of water when measured by the Karl Fischer's method.

Figure 2:
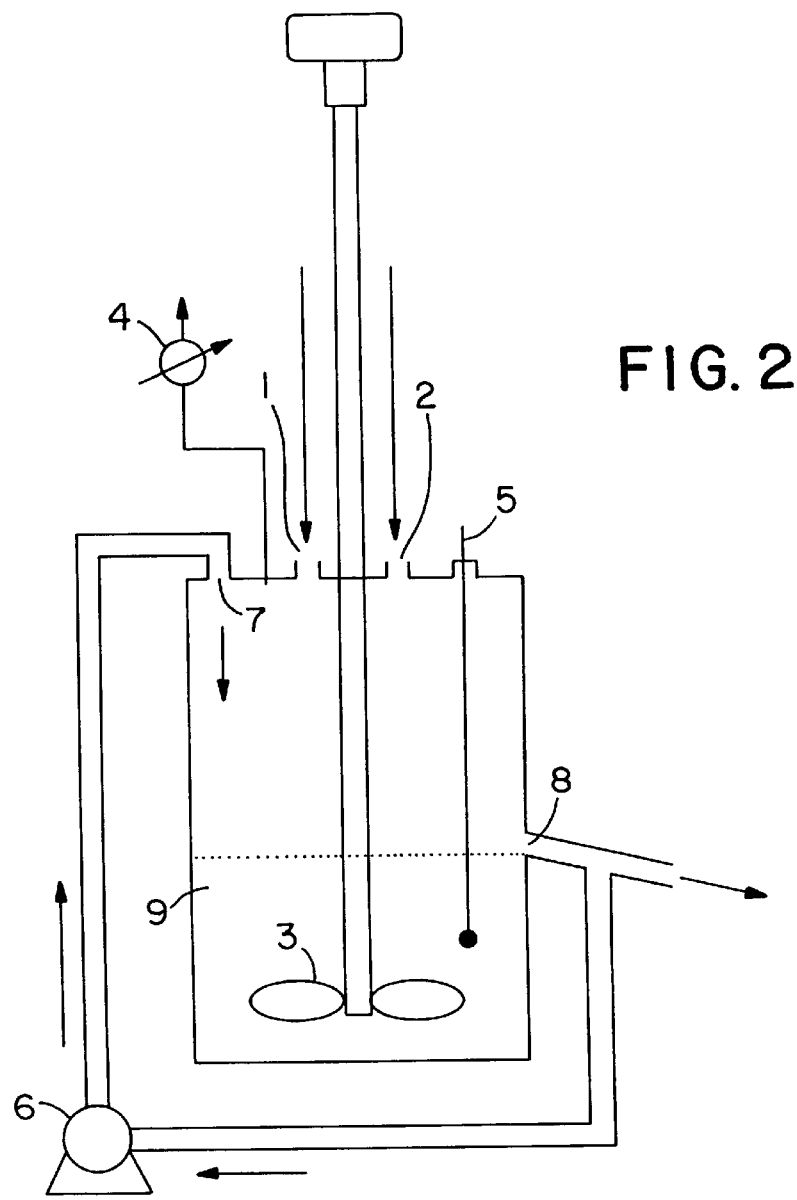
FIG. 2 is a diagram of a reactor for carrying out a bromination reaction in the present invention.
Figure 3:
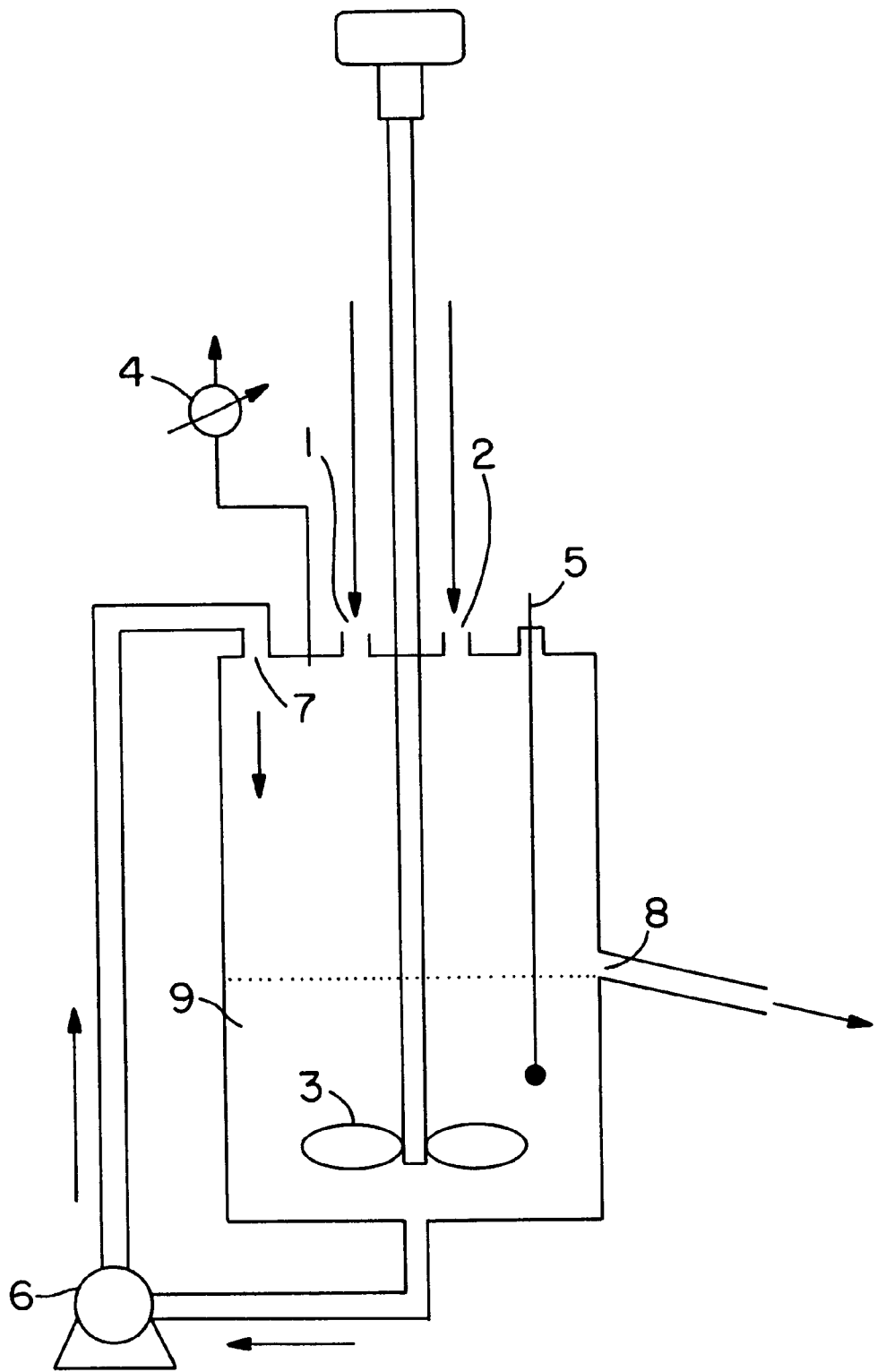
FIG. 3 is a diagram showing another example of a reactor for carrying out a bromination reaction in the present invention.

This solution and bromine were continuously charged into a glass reactor equipped with a stirrer 3, reflux condenser 4 and thermometer 5 shown in FIG. 2 from an input port 1 at a rate of $5.3 \times 10^{-3}$ l/min and from an input port 2 at a rate of $0.58 \times 10^{-3}$ l/min, respectively (molar ratio of bromine to the compound (1): 2.45). The solution mixed in the reactor generated heat due to the reaction heat of bromination and vapor produced thereby was refluxed to the reactor by the reflux condenser 4 which was fully cooled. About 20 minutes after the start of the addition of the solution of the raw material No. (1) and bromine, the reaction solution began to output from an output port 8 and then outputted continuously (residence time: 20.4 min). Part of the reaction solution in the reactor (120 ml) was circulated in the reactor at a rate of 0.03 l/min using a pump 6 from the time when the reaction solution began to output.

After excessive bromine contained in the reaction solution from the reactor was reduced by an aqueous solution of sodium bisulfite (about 15 wt %), generated hydrogen bromide was neutralized with an aqueous solution of sodium hydroxide. Thereafter, 1,000 g of ion exchange water was added to this solution and stirred, a methylene chloride layer was separated, and about 90% of methylene chloride was evaporated and removed from the methylene chloride layer. Methanol was added to precipitate a reaction product, and the precipitate was filtered off to take out a bulk solid. This bulk solid was ground with a mortar, and the ground product was dried at a temperature of 80° C. and a reduced pressure for 10 hours to obtain 2,2-bis{3,5-dibromo-4-(2,3-dibromopropyloxy)phenyl}propane. This bromine compound had a purity of 94.2% and a bromine content of 67.3% (theoretical value: 67.8%).

Example 41

A reaction was carried out in the same manner as in Example 40 except that the amount of methylene chloride was changed from 1,703 g to 4,405 g (51.8 mols) (specific gravity of the solution: 1.42, water content: 130 ppm) and the addition rate of the solution of 2,2-bis{(3,5-dibromo-4-allyloxy)phenyl}propane was changed to $10.5 \times 10^{-3}$ l/min. The obtained 2,2-bis{3,5-dibromo-4-(2,3-dibromopropyloxy)phenyl}propane had a purity of 94.2%.

Example 42

A reaction was carried out in the same manner as in Example 40 except that a mixture solvent of 900 g (10.6 mols) of methylene chloride and 803 g (6.7 mols) of chloroform was used in place of 1,703 g of methylene chloride (specific gravity of the solution: 1.48, water content: 260 ppm). The obtained 2,2-bis{3,5-dibromo-4-(2,3-dibromopropyloxy)phenyl}propane had a purity of 94.0%.

Example 43

A reaction was carried out in the same manner as in Example 40 except that the addition rate of the solution of 2,2-bis{(3,5-dibromo-4-allyloxy)phenyl}propane was changed to $135.2 \times 10^{-3}$ l/min and the addition rate of bromine was changed to $14.8 \times 10^{-3}$ l/min. The obtained 2,2-bis{3,5-dibromo-4-(2,3-dibromopropyloxy)phenyl}propane had a purity of 94.1%.

Example 44

1,043 g (1.60 mols) of 2,2-bis{(3,5-dibromo-4-isobutenyloxy)phenyl}propane (raw material No. (2)) was dissolved in 3,400 g (40.0 mols) of methylene chloride. This solution had a specific gravity of 1.46 and contained 120 ppm of water when measured by the Karl Fischer's method.

This solution and bromine were continuously charged into a glass reactor equipped with a stirrer 3, reflux condenser 4 and thermometer 5 shown in FIG. 2 from an input port 1 at a rate of $10.5 \times 10^{-3}$ l/min and from an input port 2 at a rate of $0.59 \times 10^{-3}$ l/min, respectively (molar ratio of bromine to the compound (2): 2.07). The solution mixed in the reactor generated heat due to the reaction heat of bromination and vapor produced thereby was refluxed to the reactor by the reflux condenser 4 which was fully cooled. About 11 minutes after the start of the addition of the solution of the raw material No. (2) and bromine, the reaction solution began to output from an output port 8 and then outputted continuously (residence time: 0.8 min). Part of the reaction solution in the reactor (120 ml) was circulated in the reactor at a rate of 0.03 l/min using a pump 6 from the time when the reaction solution began to output.

The reaction solution from the reactor was treated in the same manner as in Example 40 to obtain 2,2-bis{3,5-dibromo-4-(2,3-dibromo-2-methylpropyloxy)phenyl}propane. This bromine compound had a purity of 93.9%.

Example 45

476 g (0.8 mol) of bis{(3,5-dibromo-4-allyloxy)phenyl}methane (raw material No. (3)) was dissolved in a mixture solvent of 1,700 g (20.0 mols) of methylene chloride and 1,700 g (19.3 mols) of 1,4-dioxane. This solution had a specific gravity of 1.22 and contained 320 ppm of water when measured by the Karl Fischer's method.

This solution and bromine were continuously charged into a glass reactor equipped with a stirrer 3, reflux condenser 4 and thermometer 5 shown in FIG. 2 from an input port 1 at a rate of $10.6 \times 10^{-3}$ l/min and from an input port 2 at a rate of $0.43 \times 10^{-3}$ l/min, respectively (molar ratio of bromine to the compound (3): 3.13). The solution mixed in the reactor generated heat due to the reaction heat of bromination and vapor produced thereby was refluxed to the reactor by the reflux codenser 4 which was fully cooled. About 11 minutes after the start of the addition of the solution of the raw material No. (3) and bromine, the reaction solution began to output from an output port 8 and then outputted continuously (residence time: 10.9 min). Part of the reaction solution in the reactor (120 ml) was circulated in the reactor at a rate of 0.03 l/min using a pump 6 from the time when the reaction solution began to output.

The reaction solution from the reactor was treated in the same manner as in Example 40 to obtain bis{3,5-dibromo-4-(2,3-dibromo-propyloxy)phenyl)methane. This bromine compound had a purity of 93.3%.

Example 46

500 g (0.8 mol) of bis{(3,5-dibromo-4-isobutenyloxy)phenyl}methane (raw material No. (4)) was dissolved in 1,700 g (20.0 mols) of methylene chloride. This solution had a specific gravity of 1.41 and contained 160 ppm of water when measured by the Karl Fischer's method.

This solution and bromine were continuously charged into a glass reactor equipped with a stirrer 3, reflux condenser 4 and thermometer 5 shown in FIG. 2 from an input port 1 at a rate of $10.5 \times 10^{-3}$ l/min and from an input port 2 at a rate of $0.62 \times 10^{-3}$ l/min, respectively (molar ratio of bromine to the compound (4): 2.23). The solution mixed in the reactor generated heat due to the reaction heat of bromination and vapor produced thereby was refluxed to the reactor by the reflux condenser 4 which was fully cooled. About 11 minutes after the start of the addition of the solution of the raw material No. (4) and bromine, the reaction solution began to output from an output port 8 and then outputted continuously (residence time: 10.8 min). Part of the reaction solution in the reactor (120 ml) was circulated in the reactor at a rate of 0.03 l/min using a pump 6 from the time when the reaction solution began to output.

The reaction solution from the reactor was treated in the same manner as in Example 40 to obtain bis{3,5-dibromo-4-(2,3-dibromo-2-methylpropyloxy)phenyl}methane. This bromine compound had a purity of 93.5%.

Example 47

517 g (0.8 mol) of bis{(3,5-dibromo-4-allyloxy) phenyl}sulfone (raw material No. (7)) was dissolved in 1,700 g (20.0 mols) of methylene chloride. This solution had a specific gravity of 1.42 and contained 180 ppm of water when measured by the Karl Fischer's method.

This solution and bromine were continuously charged into a glass reactor equipped with a stirrer 3, reflux condenser 4 and thermometer 5 shown in FIG. 2 from an input port 1 at a rate of $10.5 \times 10^{-3}$ l/min and from an input port 2 at a rate of $0.59 \times 10^{-3}$ l/min, respectively (molar ratio of bromine to the compound (7): 2.13). The solution mixed in the reactor generated heat due to the reaction heat of bromination and vapor produced thereby was refluxed to the reactor by the reflux condenser 4 which was fully cooled. About 11 minutes after the start of the addition of the solution of the raw material No. (7) and bromine, the reaction solution began to output from an output port 8 and then outputted continuously (residence time: 10.8 min). Part of the reaction solution in the reactor (120 ml) was circulated in the reactor at a rate of 0.03 l/min using a pump 6 from the time when the reaction solution began to output.

The reaction solution from the reactor was treated in the same manner as in Example 40 to obtain bis{3,5-dibromo-4-(2,3-dibromo-propyloxy)phenyl}sulfone. This bromine compound had a purity of 92.3%.

Example 48

466 g (0.8 mol) of (3,3',5,5'-tetrabromo-4,4'-diallyloxy) biphenyl (raw material No. (5)) was dissolved in a mixture solvent of 1,700 g (20.0 mols) of methylene chloride and 1,700 g (19.3 mols) of 1,4-dioxane. This solution had a specific gravity of 1.20 and contained 320 ppm of water when measured by the Karl Fischer's method.

This solution and bromine were continuously charged into a glass reactor equipped with a stirrer 3, reflux condenser 4 and thermometer 5 shown in FIG. 2 from an input port 1 at a rate of $10.6 \times 10^{-3}$ l/min and from an input port 2 at a rate of $0.43 \times 10^{-3}$ l/min, respectively (molar ratio of bromine to the compound (5): 3.16). The solution mixed in the reactor generated heat due to the reaction heat of bromination and vapor produced thereby was refluxed to the reactor by the reflux condenser 4 which was fully cooled. About 11 minutes after the start of the addition of the solution of the raw material No. (5) and bromine, the reaction solution began to output from an output port 8 and then outputted continuously (residence time: 10.9 min). Part of the reaction solution in the reactor (120 ml) was circulated in the reactor at a rate of 0.03 l/min using a pump 6 from the time when the reaction solution began to output.

The reaction solution from the reactor was treated in the same manner as in Example 40 to obtain {3,3',5,5'-tetrabromo-4,4'-(2,3-dibromo-propyloxy)}biphenyl. This bromine compound had a purity of 93.0%.

Example 49

A reaction was carried out in the same manner as in Example 40 except that the addition rate of the solution of 2,2-bis{(3,5-dibromo-4-allyloxy)phenyl}propane was changed to $0.57 \times 10^{-3}$ l/min and the addition rate of bromine was changed to $0.062 \times 10^{-3}$ l/min. The obtained 2,2-bis{3,5-dibromo-4-(2,3-dibromopropyloxy)phenyl}propane had a purity of 94.1%.

Comparative Example 3

A reaction was carried out for 40 minutes in the same manner as in Example 40 except that the addition rate of the solution of 2,2-bis{(3,5-dibromo-4-allyloxy) phenyl}propane was fixed at $5.3 \times 10^{-3}$ l/min, bromine was added continuously at a rate of $0.28 \times 10^{-3}$ l/min for the first 10 minutes (molar ratio of bromine to raw material No. (1): 1.18) and at a rate of $0.84 \times 10^{-3}$ l/min for the next 10 minutes (molar ratio of bromine to raw material No. (1): 3.55), and this cycle was repeated. About 20 minutes after the start of the addition of the solution of the raw material No. (1) and bromine, the reaction solution began to output from an output port 8 and then outputted continuously (residence time: 20.5 min). Part of the reaction solution in the reactor (120 ml) was circulated in the reactor at a rate of 0.03 l/min using a pump 6 from the time when the reaction solution began to output.

The reaction solution from the reactor was treated in the same manner as in Example 40 to obtain 2,2-bis{(3,5-dibromo-4-allyloxy)phenyl}propane. This bromine compound had a purity of 85.0% and was powders having low storage stability that they were easily adhered to one another.

Comparative Example 4

A reaction was carried out in the same manner as in Example 40 except that the addition rate of the solution of 2,2-bis{(3,5-dibromo-4-allyloxy)phenyl}propane was changed to $5.3 \times 10^{-3}$ l/min and the addition rate of bromine was changed to $0.4 \times 10^{-3}$ l/min (molar ratio of bromine to raw material No. (1): 1.69), and the reaction solution was treated in the same manner as in Example 40 to obtain 2,2-bis{3,5-dibromo-4-(2,3-dibromopropyloxy) phenyl}propane. This bromine compound had a purity of 71.0% and were powders having low storage stability that they were easily adhered to one another.

Comparative Example 5

1,000 g (1.6 mols) of 2,2-bis{(3,5-dibromo-4-allyloxy) phenyl}propane was dissolved in 1,703 g (20.0 mols) of methylene chloride. 1,694 g of this solution was charged into a 3,000 ml glass reactor equipped with a stirrer, reflux condenser, thermometer and dropping funnel, and 396 g of bromine was added dropwise gradually from the dropping funnel in 220 minutes under agitation. At the start of the addition of bromine, the temperature of the solution was 20° C. but was gradually increased by reaction heat along with the addition of bromine and reached 37° C. at the end of addition. The reactor was not cooled and the reflux of methylene chloride did not occur while bromine was added.

After the end of the addition of bromine, the reaction solution was treated in the same manner as in Example 40 to obtain 2,2-bis{3,5-dibromo-4-(2,3-dibromopropyloxy) phenyl}propane. This bromine compound had a low purity of 82.1%, colored outer appearance and low storage stability that they were easily adhered to one another.

The results of Example 40 to 49 and Comparative Examples 3 and 4 are shown in Table 9 and Table 10.

In Table 9 and Table 10, the solvents (A) to (C) are:
(A) methylene chloride
(B) methylene chloride/chloroform=53/47 (weight ratio)
(C) methylene chloride/1,4-dioxane=50/50 (weight ratio)

The concentration of water is expressed in mol % based on the number of mols of the unsaturated groups of a raw material compound.

solution output from the static mixer was charged into a 30 liter agitation tank equipped with a reflux condenser. In this agitation tank, reaction heat was radiated and vapor produced thereby was refluxed to suppress the scattering of bromine. Subsequently, the mixture solution was stirred in the agitation tank, was caused to stay in the agitation tank for about 5 minutes and then discharged from the overflow port of the agitation tank.

After about 10 ml of the reaction solution flowing out from the overflow port was collected and excess bromine was reduced with 5 g of a 15 wt % aqueous solution of sodium bisulfite, it was neutralized with a 25 wt % aqueous solution of caustic soda. Most of methylene chloride was evaporated and removed from the obtained methylene chloride layer, 50 ml of methanol was added to precipitate a reaction product, and the precipitate was filtered off to take

TABLE 9

|  | Ex. 40 | Ex. 41 | Ex. 42 | Ex. 43 | Ex. 44 | Ex. 45 |
|---|---|---|---|---|---|---|
| raw material compound (raw material No.) | (1) | (1) | (1) | (1) | (2) | (3) |
| amount of raw material (mol) | 1.60 | 1.60 | 1.60 | 1.60 | 1.60 | 0.80 |
| solvent | (A) | (A) | (B) | (A) | (A) | (C) |
| addition rate of raw material compound solution ($\times 10^{-3}$ l/min) | 5.3 | 10.5 | 5.3 | 135.2 | 10.5 | 10.6 |
| addition rate of bromine ($\times 10^{-3}$ l/min) | 0.58 | 0.58 | 0.58 | 14.8 | 0.59 | 0.43 |
| residence time (min) | 20.4 | 10.8 | 20.4 | 0.8 | 10.8 | 10.9 |
| concentration of water (mol %) | 0.75 | 1.2 | 1.2 | 0.75 | 0.93 | 4.3 |
| molar ratio of bromine/raw material compound | 2.45 | 2.54 | 2.42 | 2.45 | 2.07 | 3.13 |
| ratio of solvent/raw material compound (molecules/unsaturated group) | 6.25 | 16.2 | 5.4 | 6.25 | 12.5 | 24.55 |
| Purity (%) | 94.2 | 94.2 | 94.0 | 94.1 | 93.9 | 93.3 |

TABLE 10

|  | Ex. 46 | Ex. 47 | Ex. 48 | Ex. 49 | C. Ex. 3 | C. Ex. 4 |
|---|---|---|---|---|---|---|
| raw material compound (raw material No.) | (4) | (7) | (5) | (1) | (1) | (1) |
| amount of raw material (mol) | 0.80 | 0.80 | 0.80 | 1.60 | 1.60 | 1.60 |
| solvent | (A) | (A) | (C) | (A) | (A) | (A) |
| addition rate of raw material compound solution ($\times 10^{-3}$ l/min) | 10.5 | 10.5 | 10.6 | 0.57 | 5.3 | 5.3 |
| addition rate of bromine ($\times 10^{-3}$ l/min) | 0.62 | 0.59 | 0.43 | 0.062 | 0.28 0.84 | 0.40 |
| residence time (min) | 10.8 | 10.8 | 10.9 | 190 | 20.5 | 21.1 |
| concentration of water (mol %) | 1.2 | 1.4 | 4.3 | 0.75 | 0.75 | 0.75 |
| molar ratio of bromine/raw material compound | 2.23 | 2.13 | 3.16 | 2.44 | 1.18 3.55 | 1.69 |
| ratio of solvent/raw material compound (molecules/unsaturated group) | 12.5 | 12.5 | 24.55 | 6.25 | 6.25 | 6.25 |
| Purity (%) | 93.5 | 92.3 | 93.0 | 94.1 | 85.0 | 71.0 |

Example 50

50 kg of a methylene chloride solution containing 18.5 kg of 2,2-bis{(3,5-dibromo-4-allyloxy)phenyl}propane was prepared in advance (specific gravity of the solution: 1.47, water content: 150 ppm).

The above prepared methylene chloride solution and bromine were introduced continuously into a static mixer having 12 elements with an inner volume of 20 cm³ (cross section: 0.5 cm²) at a rate of 133.9 g/sec (91.1 ml/sec) and at a rate of 25.7 g/sec (8.3 ml/sec), respectively, that is, the flow rate of the mixture solution became 199 cm/sec {about (91.1+8.3)/0.5), and mixed together [residence time in the static mixer: 0.20 sec {about 20/(91.1+8.3)}]. The mixture out a bulk solid. This bulk solid was ground with a mortar, and the ground product was dried at a temperature of 80° C. and a reduced pressure for 3 hours to obtain 1.7 g of a product.

When the obtained product was analyzed by $^1$H-NMR, a signal derived from —CHBr— was observed at 4.51 to 4.53 ppm and a signal derived from —CH$_2$Br was observed at 3.94 to 4.09 ppm. It was confirmed from FT-IR analysis that the absorption of —O—CH$_2$— was observed and the absorption of an allyl group was not observed. It was confirmed from the results of the above analyses that the product was 2,2-bis{3,5-dibromo-4-(2,3-dibromopropyloxy)phenyl}propane. This bromine compound had a purity of 96.3%, a melting point of 114° C. and a bromine content of 67.5% (theoretical value: 67.8%).

Example 51

A reaction was carried out in the same manner as in Example 50 except that a static mixer having 6 elements with an inner volume of 10 cm$^3$ (cross section: 0.5 cm$^2$) was used in place of the static mixer having 12 elements with an inner volume of 20 cm$^2$ (cross section: 0.5 cm$^2$) (residence time in the static mixer: 0.10 sec). When the reaction product was analyzed in the same manner as in Example 50, it was confirmed that the product was 2,2-bis(3,5-dibromo-4-(2,3-dibromopropyloxy)phenyl}propane. This bromine compound had a purity of 96.3%, a melting point of 114° C. and a bromine content of 67.5% (theoretical value: 67.8%).

Example 52

40 kg of a methylene chloride solution containing 14.8 kg of 2,2-bis{(3,5-dibromo-4-isobutenyloxy)phenyl}propane was prepared in advance (specific gravity of the solution: 1.47, water content: 150 ppm).

The above prepared methylene chloride solution and bromine were introduced continuously into the same static mixer as used in Example 50 at a rate of 98.9 g/sec (67.3 ml/sec) and at a rate of 22.4 g/sec (7.2 ml/sec), respectively, that is, the flow rate of the mixture solution became 149 cm/sec, and mixed together (residence time in the static mixer: 0.27 sec). The mixture solution output from the static mixer was charged into a 23 liter agitation tank equipped with a reflux condenser. In this agitation tank, reaction heat was radiated and vapor produced thereby was refluxed to suppress the scattering of bromine. Subsequently, the mixture solution was stirred in the agitation tank, was caused to stay in the agitation tank for about 5 minutes and then discharged from the overflow port of the agitation tank.

This reaction solution was treated in the same manner as in Example 50 to obtain 1.6 g of a reaction product. When the obtained product was analyzed by $^1$H-NMR and FT-IR as in Example 50, it was confirmed that the product was 2,2-bis{3,5-dibromo-4-(2,3-dibromo-2-methylpropyloxy) phenyl}propane. This bromine compound had a purity of 94.0% and a bromine content of 65.3% (theoretical value: 65.8%).

Example 53

40 kg of a methylene chloride solution containing 14.8 kg of bis{(3,5-dibromo-4-allyloxy)phenyl}methane was prepared in advance (specific gravity of the solution: 1.47, water content: 200 ppm).

The above prepared methylene chloride solution and bromine were introduced continuously into the same static mixer as used in Example 50 at a rate of 79.8 g/sec (54.3 ml/sec) and at a rate of 16.6 g/sec (5.4 ml/sec), respectively, that is, the flow rate of the mixture solution became 119 cm/sec, and mixed together (residence time in the static mixer: 0.34 sec). The mixture solution output from the static mixer was charged into a 28 liter agitation tank equipped with a reflux condenser. In this agitation tank, reaction heat was radiated and vapor produced thereby was refluxed to suppress the scattering of bromine. Subsequently, the mixture solution was stirred in the agitation tank, was caused to stay in the agitation tank for about 8 minutes and then discharged from the overflow port of the agitation tank.

This reaction solution was treated in the same manner as in Example 50 to obtain 1.8 g of a reaction product. When the obtained product was analyzed by $^1$H-NMR and FT-IR as in Example 50, it was confirmed that the product was bis{3,5-dibromo-4-(2,3-dibromo-propyloxy) phenyl}methane. This bromine compound had a purity of 91.8% and a bromine content of 69.1% (theoretical value: 69.8%).

Example 54

40 kg of a solution of 14.8 kg of bis{(3,5-dibromo-4-isobutenyloxy)phenyl}methane dissolved in a mixture solvent of methylene chloride and 1,4-dioxane (weight ratio of methylene chloride to 1,4-dioxane=70/30) was prepared in advance (specific gravity of the solution: 1.35, water content: 250 ppm).

The above prepared mixture solvent solution and bromine were introduced continuously into the same static mixer as used in Example 50 at a rate of 126.8 g/sec (93.9 ml/sec) and at a rate of 28.8 g/sec (9.3 ml/sec), respectively, that is, the flow rate of the mixture solution became 206 cm/sec, and mixed together (residence time in the static mixer: 0.19 sec). The mixture solution output from the static mixer was charged into a 30 liter agitation tank equipped with a reflux condenser. In this agitation tank, reaction heat was radiated and vapor produced thereby was refluxed to suppress the scattering of bromine. Subsequently, the mixture solution was stirred in the agitation tank, was caused to stay in the agitation tank for about 5 minutes and then discharged from the overflow port of the agitation tank.

This reaction solution was treated in the same manner as in Example 50 to obtain 1.8 g of a reaction product. When the obtained product was analyzed by $^1$H-NMR and FT-IR as in Example 50, it was confirmed that the product was bis{3,5-dibromo-4-(2,3-dibromo-2-methylpropyloxy) phenyl)methane. This bromine compound had a purity of 92.0% and a bromine content of 67.0% (theoretical value: 67.7%).

Example 55

30 kg of a solution of 11.1 kg of (3,3',5,5'-tetrabromo-4, 4'-diallyloxy)biphenyl dissolved in a mixture solvent of methylene chloride and 1,4-dioxane (weight ratio of methylene chloride to 1,4-dioxane=70/30) was prepared in advance (specific gravity of the solution: 1.35, water content: 250 ppm).

The above prepared mixture solvent solution and bromine were introduced continuously into the same static mixer as used in Example 50 at a rate of 140.0 g/sec (103.7 ml/sec) and at a rate of 28.8 g/sec (9.3 ml/sec), respectively, that is, the flow rate of the mixture solution became 226 cm/sec, and mixed together (residence time in the static mixer: 0.18 sec). The mixture solution output from the static mixer was charged into a 20 liter agitation tank equipped with a reflux condedser. In this agitation tank, reaction heat was radiated and vapor produced thereby was refluxed to suppress the scattering of bromine. Subsequently, the mixture solution was stirred in the agitation tank, was caused to stay in the agitation tank for about 3 minutes and then discharged from the overflow port of the agitation tank.

This reaction solution was treated in the same manner as in Example 50 to obtain 1.5 g of a reaction product. When the obtained product was analyzed by $^1$H-NMR and FT-IR as in Example 50, it was confirmed that the product was (3,3',5,5'-tetrabromo-4,4'-(2,3-dibromo-propyloxy) }biphenyl. This bromine compound had a purity of 93.5% and a bromine content of 70.0% (theoretical value: 70.9%).

Example 56

40 kg of a methylene chloride solution containing 14.8 kg of bis{(3,5-dibromo-4-allyloxy)phenyl}sulfone was prepared in advance (specific gravity of the solution: 1.47, water content: 600 ppm).

The above prepared methylene chloride solution and bromine were introduced continuously into the same static mixer as used in Example 51 at a rate of 99.3 g/sec (67.6 ml/sec) and at a rate of 28.8 g/sec (9.3 ml/sec), respectively, that is, the flow rate of the mixture solution became 154 cm/sec, and mixed together (residence time in the static mixer: 0.13 sec). The mixture solution output from the static mixer was charged into a 15 liter agitation tank equipped with a reflux condenser. In this agitation tank, reaction heat was radiated and vapor produced thereby was refluxed to suppress the scattering of bromine. Subsequently, the mixture solution was stirred in the agitation tank, was caused to stay in the agitation tank for about 3 minutes and then discharged from the overflow port of the agitation tank.

This reaction solution was treated in the same manner as in Example 50 to obtain 1.5 g of a reaction product. When the obtained product was analyzed by $^1$H-NMR and FT-IR as in Example 50, it was confirmed that the product was {3,3',5,5'-tetrabromo-4,4'-(2,3-dibromo-propyloxy)}sulfone. This bromine compound had a purity of 91.0% and a bromine content of 63.9% (theoretical value: 66.2%).

The results of Examples 50 to 56 are shown in Table 11.

120 minutes at a temperature of 15° C. while the resulting solution was stirred. After the end of addition, the reaction solution was kept stirred at a temperature of 15° C. for 30 minutes to terminate the addition reaction of bromine. When 10 ml of this reaction solution was dispensed by a hole pipette and the amount of residual bromine contained in the bromine compound solution was measured, it was found to be 3.60 g/l.

Preparation Example 3

A bromination reaction was carried out in the same manner as in Preparation Example 1 except that 2,820 g (4.33 mols) of 2,2-bis{(3,5-dibromo-4-isobutenyloxy)phenyl}propane was used in place of 2,700 g of 2,2-bis{(3,5-dibromo-4-allyloxy)phenyl}propane. When the amount of residual bromine contained in the bromine compound solution was measured, it was found to be 3.05 g/l.

Preparation Example 4

A bromination reaction was carried out in the same manner as in Preparation Example 1 except that 2,580 g (4.33 mols) of bis{(3,5-dibromo-4-allyloxy)phenyl}methane was used in place of 2,700 g of 2,2-bis{(3,5-dibromo-4-allyloxy)phenyl}propane. When the amount

TABLE 11

|  | Ex. 50 | Ex. 51 | Ex. 52 | Ex. 53 | Ex. 54 | Ex. 55 | Ex. 56 |
| --- | --- | --- | --- | --- | --- | --- | --- |
| raw material compound (raw material No.) | (1) | (1) | (2) | (3) | (4) | (5) | (7) |
| addition rate of raw material compound solution (g/sec) | 133.9 | 133.9 | 98.9 | 79.8 | 126.8 | 140.0 | 99.3 |
| addition rate of bromine (g/sec) | 25.7 | 25.7 | 22.4 | 16.6 | 28.8 | 28.8 | 28.8 |
| flow rate of mixture solution (cm/sec) | 199 | 199 | 149 | 119 | 206 | 226 | 154 |
| number of elements | 12 | 6 | 12 | 12 | 12 | 12 | 6 |
| residence time (sec) | 0.20 | 0.10 | 0.27 | 0.34 | 0.19 | 0.18 | 0.13 |
| molar ratio of bromine/raw material compound | 2.02 | 2.02 | 2.50 | 2.10 | 2.40 | 2.02 | 3.17 |
| concentration of water (mol %) | 0.7 | 0.7 | 0.7 | 0.9 | 1.2 | 1.1 | 2.9 |
| Purity (%) | 96.3 | 96.3 | 94.0 | 91.8 | 92.0 | 93.5 | 91.0 |

Preparation Example 1

2,700 g (4.33 mols) of 2,2-bis{(3,5-dibromo-4-allyloxy)phenyl}propane and 4,600 g of methylene chloride dehydrated by synthetic zeolite were charged into a 10 liter glass reactor equipped with a stirrer, reflux condenser, thermometer and dropping funnel and dissolved. 1,394 g (8.72 mols) of bromine was added dropwise from the dropping funnel in 8 minutes while the resulting solution was stirred and methylene chloride was refluxed at a temperature of 39 to 41° C. After the end of addition, the reaction solution was kept stirred for 30 minutes while methylene chloride was refluxed at a temperature of 39 to 41° C. to terminate the addition reaction of bromine. When 10 ml of this reaction solution was dispensed by a hole pipette and the amount of residual bromine contained in the bromine compound solution was measured, it was found to be 3.68 g/l.

Preparation Example 2

2,700 g (4.33 mols) of 2,2-bis{(3,5-dibromo-4-allyloxy)phenyl}propane and 460 g of chlorobenzene dehydrated by synthetic zeolite were charged into a 10 liter glass reactor equipped with a stirrer, reflux condenser, thermometer and dropping funnel and dissolved. 1,394 g (8.72 mols) of bromine was added dropwise from the dropping funnel in of residual bromine contained in the bromine compound solution was measured, it was found to be 3.05 g/l.

Example 57

12.5 g (3.7 mols of sodium hydrogen sulfite based on 1 mol of bromine) of a 15.6 wt % aqueous solution of sodium hydrogen sulfite was added to 328 g of the bromine compound solution obtained in Preparation Example 1, 3.8 g (4.7 mols of sodium hydroxide based on 1 mol of bromine) of a 25 wt % aqueous solution of sodium hydroxide was added immediately, and 300 g of water was further added to ensure that the weight ratio of a methylene chloride phase to a water phase should be almost 1:1 and stirred at 20° C. for 30 minutes. After the end of agitation, the methylene chloride phase was separated from the water phase, the water phase was removed, and 100 ml of water was added to the methylene chloride phase and stirred for 15 minutes to clean the methylene chloride phase. The pH of the water phase was 7.2 and bromine was not detected in both phases.

Thereafter, 100 ml of the methylene chloride phase which had been reduced and neutralized was collected, about 90% of methylene chloride was evaporated and removed from the methylene chloride phase, 250 ml of methanol was added to precipitate a reaction product, and the precipitate was filtered off to take out a bulk solid. This bulk solid was ground with a mortar, and the ground product was dried at a temperature of 80° C. and a reduced pressure of 5 mmHg for 3 hours to obtain 114.7 g of a product.

When the obtained product was analyzed by $^1$H-NMR, a signal derived from —CHBr— was observed at 4.51 to 4.53 ppm and a signal derived from —CH$_2$Br was observed at 3.94 to 4.09 ppm. It was confirmed from FT-IR analysis that the absorption of —O—CH$_2$— was observed and the absorption of an allyl group was not observed. It was confirmed from the results of the above analyses that the product was 2,2-bis{3,5-dibromo-4-(2,3-dibromopropyloxy)phenyl}propane. When 1 g of this bromine compound was added to 10 g of water and stirred at 20° C. for 24 hours and then the bromine compound was filtered off to measure the bromine concentration of a water phase, bromine was not detected.

Example 58

Reduction and neutralization were carried out in the same manner as in Example 57 except that the amount of the 15.6 wt % aqueous solution of sodium hydrogen sulfite was changed to 12.5 g to 24.5 g (7.3 mols of sodium hydrogen sulfite based on 1 mol of bromine) and the amount of the 25 wt % aqueous solution of sodium hydroxide was changed from 3.8 g to 13.1 g (16.3 mols of sodium hydroxide based on 1 mol of bromine). A methylene chloride phase was separated from a water phase, the water phase was removed, and 100 ml of water was added to the methylene chloride phase and stirred for 15 minutes to clean the methylene chloride phase. The pH of the water phase was 7.2, and bromine was not detected in both phases.

2,2-bis{3,5-dibromo-4-(2,3-dibromopropyloxy) phenyl}propane was obtained from the methylene chloride phase in the same manner as in Example 57. When 1 g of this bromine compound was added to 10 g of water and stirred at 20° C. for 24 hours and then the bromine compound was filtered off to measure the bromine concentration of the water phase, bromine was not detected.

Example 59

Reduction and neutralization were carried out in the same manner as in Example 57 except that 9.7 g (3.3 mols of oxalic acid based on 1 mol of bromine) of a 15.6 wt % aqueous solution of oxalic acid was used in place of 12.5 g of the 15.6 wt % aqueous solution of sodium hydrogen sulfite. A methylene chloride phase was separated from a water phase, the water phase was removed, and 100 ml of water was added to the methylene chloride phase and stirred for 15 minutes to clean the methylene chloride phase. The pH of the water phase was 7.2, and bromine was not detected in both phases.

2,2-bis{3,5-dibromo-4-(2,3-dibromopropyloxy) phenyl}propane was obtained from the methylene chloride phase in the same manner as in Example 57. When 1 g of this bromine compound was added to 10 g of water and stirred at 20° C. for 24 hours and then the bromine compound was filtered off to measure the bromine concentration of the water phase, bromine was not detected.

Example 60

Reduction and neutralization were carried out in the same manner as in Example 57 except that 7.1 g (3.2 mols of sodium nitrite based on 1 mol of bromine) of a 15.6 wt % aqueous solution of sodium nitrite was used in place of 12.5 g of the 15.6 wt % aqueous solution of sodium hydrogen sulfite. A methylene chloride phase was separated from a water phase, the water phase was removed, and 100 ml of water was added to the methylene chloride phase and stirred for 15 minutes to clean the methylene chloride phase. The pH of the water phase was 7.2, and bromine was not detected in both phases.

2,2-bis{3,5-dibromo-4-(2,3-dibromopropyloxy) phenyl}propane was obtained from the methylene chloride phase in the same manner as in Example 57. When 1 g of this bromine compound was added to 10 g of water and stirred at 20° C. for 24 hours and then the bromine compound was filtered off to measure the bromine concentration of the water phase, bromine was not detected.

Example 61

12.5 g (3.0 mols of sodium hydrogen sulfite based on 1 mol of bromine) of a 15.6 wt % aqueous solution of sodium hydrogen sulfite was added to 328 g of the bromine compound solution obtained in Preparation Example 2, 3.8 g (3.9 mols of sodium hydroxide based on 1 mol of bromine) of a 25 wt % aqueous solution of sodium hydroxide was added immediately, and 300 g of water was further added to ensure that the weight ratio of a chlorobenzene phase to a water phase should be almost 1:1 and stirred at 20° C. for 30 minutes. After the end of agitation, the chlorobenzene phase was separated from the water phase, the water phase was removed, and 100 ml of water was added to the chlorobenzene phase and stirred for 15 minutes to clean the chlorobenzene phase. The pH of the water phase was 7.2 and bromine was not detected in both phases.

Thereafter, 100 ml of the chlorobenzene phase which had been reduced and neutralized was collected, about 90% of chlorobenzene was evaporated and removed from the chlorobenzene phase, 250 ml of methanol was added to precipitate a reaction product, and the precipitate was filtered off to take out a bulk solid. This bulk solid was ground with a mortar, and the ground product was dried at a temperature of 80° C. and a reduced pressure of 5 mmHg for 3 hours to obtain 2,2-bis{3,5-dibromo-4-(2,3-dibromopropyloxy) phenyl}propane. When 1 g of this bromine compound was added to 10 g of water and stirred at 20° C. for 24 hours and then the bromine compound was filtered off to measure the bromine concentration of the water phase, bromine was not detected.

Example 62

13.0 g (4.7 mols of sodium hydrogen sulfite based on 1 mol of bromine) of a 15.6 wt % aqueous solution of sodium hydrogen sulfite was added to 324 g of the bromine compound solution obtained in Preparation Example 3, 4.0 g (6.1 mols of sodium hydroxide based on 1 mol of bromine) of a 25 wt % aqueous solution of sodium hydroxide was added immediately, and 300 g of water was further added to ensure that the weight ratio of a methylene chloride phase to a water phase should be almost 1:1 and stirred at 20° C. for 30 minutes. After the end of agitation, the methylene chloride phase was separated from the water phase, the water phase was removed, and 100 ml of water was added to the methylene chloride phase and stirred for 15 minutes to clean the methylene chloride phase. The pH of the water phase was 7.2, and bromine was not detected in both phases.

Thereafter, 100 ml of the methylene chloride phase which had been reduced and neutralized was collected, about 90% of methylene chloride was evaporated and removed from the methylene chloride phase, 250 ml of methanol was added to precipitate a reaction product, and the precipitate was filtered off to take out a bulk solid. This bulk solid was ground with a mortar, and the ground product was dried at a temperature of 80° C. and a reduced pressure of 5 mmHg for 3 hours to obtain 2,2-bis{3,5-dibromo-4-(2,3-dibromo-2-methylpropyloxy)phenyl}propane. When 1 g of this bromine compound was added to 10 g of water and stirred at 20° C. for 24 hours and then the bromine compound was filtered off to measure the bromine concentration of the water phase, bromine was not detected.

Example 63

12.5 g (4.5 mols of sodium hydrogen sulfite based on 1 mol of bromine) of a 15.6 wt % aqueous solution of sodium hydrogen sulfite was added to 328 g of the bromine compound solution obtained in Preparation Example 4, 3.9 g (5.8 mols of sodium hydroxide based on 1 mol of bromine) of a 25 wt % aqueous solution of sodium hydroxide was added immediately, and 300 g of water was further added to ensure that the weight ratio of a methylene chloride phase to a water phase should be almost 1:1 and stirred at 20° C. for 30 minutes. After the end of agitation, the methylene chloride phase was separated from the water phase, the water phase was removed, and 100 ml of water was added to the methylene chloride phase and stirred for 15 minutes to clean the methylene chloride phase. The pH of the water phase was 7.2, and bromine was not detected in both phases.

Thereafter, 100 ml of the methylene chloride phase which had been reduced and neutralized was collected, about 90% of methylene chloride was evaporated and removed from the methylene chloride phase, 250 ml of methanol was added to precipitate a reaction product, and the precipitate was filtered off to take out a bulk solid. This bulk solid was ground with a mortar, and the ground product was dried at a temperature of 80° C. and a reduced pressure of 5 mmHg for 3 hours to obtain bis(3,5-dibromo-4-(2,3-dibromopropyloxy)phenyl}methane. When 1 g of this bromine compound was added to 10 g of water and stirred at 20° C. for 24 hours and then the bromine compound was filtered off to measure the bromine concentration of the water phase, bromine was not detected.

Example 64

The methylene chloride solution prepared in Preparation Example 1 and a 15.6 wt % aqueous solution of sodium hydrogen sulfite were introduced continuously into a static mixer having 12 elements with an inner volume of 20 cm$^3$ (cross section: 0.5 cm$^2$) at a rate of 10.7 g/sec (7.2 ml/sec) and at a rate of 0.4 g/sec (0.38 ml/sec), respectively, that is, the flow rate of the mixture solution became 15.3 cm/sec, and mixed together (residence time in the static mixer: 2.6 sec, 3.7 mols of sodium hydrogen sulfite based on 1 mol of bromine). The mixture solution was then charged into a 30 liter agitation tank having a valve in the bottom portion. Subsequently, the mixture solution was stirred in the agitation tank and was caused to stay in the agitation tank for about 10 minutes, and then part of the mixture solution was taken out from the bottom portion of the agitation tank. When the bromine concentration of the methylene chloride phase was measured, bromine was not detected.

14 liters of the mixture solution which was taken out from the bottom portion of the agitation tank and reduced was added to 3,000 g of a 2.5 wt % aqueous solution of sodium hydroxide while violently stirred (5.9 mols of sodium hydroxide based on 1 mol of bromine). This agitation was carried out for 20 minutes. After the end of agitation, a methylene chloride phase was separated from a water phase, the water phase was removed, and 2,000 g of purified water was added to the methylene chloride phase and stirred for 20 minutes to clean the methylene chloride phase. The time required to terminate reduction and neutralization reactions was about 1 hour.

Example 65

The procedure of Example 64 was repeated except that a static mixer having 18 elements with an inner volume of 30 cm$^3$ (cross section: 0.5 cm$^2$) was used in place of the static mixer having 12 elements with an inner volume of 20 cm$^3$ of Example 64 (cross section: 0.5 cm$^2$), the concentration of the aqueous solution of sodium hydrogen sulfite was changed to 5.2 wt %, and the addition rate of the solution was changed to 0.8 g/sec (0.75 ml/sec) (flow rate of the mixture solution: 15.9 cm/sec, residence time in the static mixer: 3.8 sec, 2.5 mols of sodium hydrogen sulfite based on 1 mol of bromine). When the bromine concentration of the methylene chloride solution phase after a reduction reaction was measured in the same manner as in Example 64, bromine was not detected.

Example 66

The procedure of Example 64 was repeated except that a static mixer having 18 elements with an inner volume of 30 cm$^3$ (cross section: 0.5 cm$^2$) was used in place of the static mixer having 12 elements with an inner volume of 20 cm$^3$ of Example 64 (cross section: 0.5 cm$^2$), the addition rate of the methylene chloride solution was changed to 26.9 g/sec (18.2 ml/sec), and the addition rate of the aqueous solution of sodium hydrogen sulfite was changed to 1.04 g/sec (0.95 ml/sec) (flow rate of the mixture solution: 38.3 cm/sec, residence time in the static mixer: 1.5 sec, 3.7 mols of sodium hydrogen sulfite based on 1 mol of bromine). When the bromine concentration of the methylene chloride solution phase after a reduction reaction was measured in the same manner as in Example 64, bromine was not detected.

Example 67

The procedure of Example 64 was repeated except that the addition rate of the aqueous solution of sodium hydrogen sulfite was changed to 0.8 g/sec (0.75 ml/sec) (flow rate of the mixture solution: 16.0 cm/sec, residence time in the static mixer: 2.6 sec, 7.4 mols of sodium hydrogen sulfite based on 1 mol of bromine). When the bromine concentration of the methylene chloride solution phase after a reduction reaction was measured in the same manner as in Example 64, bromine was not detected.

Example 68

The procedure of Example 64 was repeated except that the chlorobenzene solution prepared in Preparation Example 2 was used in place of the methylene chloride solution prepared in Preparation Example 1 and the addition rate of the chlorobenzene solution was set to 10.9 g/sec (9.9 ml/sec) (flow rate of the mixture solution: 20.7 cm/sec, residence time in the static mixer: 1.9 sec, 3.0 mols of sodium hydrogen sulfite based on 1 mol of bromine). When the bromine concentration of the chlorobenzene solution phase after a reduction reaction was measured in the same manner as in Example 64, bromine was not detected.

Example 69

The procedure of Example 64 was repeated except that the methylene chloride solution prepared in Preparation Example 4 was used in place of the methylene chloride solution prepared in Preparation Example 1 (flow rate of the mixture solution: 15.2 cm/sec, residence time in the static mixer: 2.7 sec, 3.7 mols of sodium hydrogen sulfite based on 1 mol of bromine). When the bromine concentration of the methylene chloride solution phase after a reduction reaction was measured in the same manner as in Example 64, bromine was not detected.

Example 70

The procedure of Example 64 was repeated except that the addition rate of the methylene chloride solution was changed to 5.4 g/sec (3.6 ml/sec) and the addition rate of the aqueous solution of sodium hydrogen sulfite was changed to 0.2 g/sec (0.19 ml/sec) (flow rate of the mixture solution: 7.6 cm/sec, residence time in the static mixer: 5.3 sec, 3.7 mols of sodium hydrogen sulfite based on 1 mol of bromine). When the bromine concentration of the methylene chloride solution phase after a reduction reaction was measured in the same manner as in Example 64, bromine was not detected.

Example 71

The procedure of Example 64 was repeated except that a 15.6 wt % aqueous solution of sodium dithionite was used in place of the aqueous solution of sodium hydrogen sulfite and the addition rate of the solution was set to 0.4 g/sec (0.38 ml/sec) (flow rate of the mixture solution: 15.2 cm/sec, residence time in the static mixer: 2.6 sec, 2.5 mols of sodium dithionite based on 1 mol of bromine). When the bromine concentration of the methylene chloride solution phase after a reduction reaction was measured in the same manner as in Example 64, bromine was not detected.

What is claimed is:

1. A method for the production of a bromine compound comprising reacting in a reactor a compound having an aliphatic unsaturated bond represented by the following formula (1) with bromine:

$$R^1—O—Ar^1—Y-Ar^2—O—R^2 \quad (2)$$

wherein $Ar^1$ and $Ar^2$ may be the same or different and are each an aromatic hydrocarbon group having 5 to 16 carbon atoms or saturated alicyclic hydrocarbon group having 5 to 12 carbon atoms, the $Ar^1$ and the $Ar^2$ hydrocarbon groups can be substituted by at least one halogen; Y is a saturated hydrocarbon group having 1 to 6 carbon atoms, sulfone group, sulfide group, ketone group, alkylene oxide group having 2 to 6 carbon atoms or single bond; $R^1$ and $R^2$ may be the same or different and are each a hydrocarbon group having 2 to 11 carbon atoms having at least one aliphatic unsaturated group, to produce a bromine compound represented by the following general formula (2):

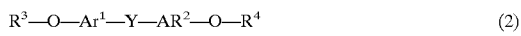

$$R^3—O—Ar^1—Y—AR^2—O—R^4 \quad (2)$$

wherein $Ar^1$, $Ar^2$ and Y are the same as defined in the above formula (1), and $R^3$ and $R^4$ are groups obtained by saturating the unsaturated groups of $R^1$ and $R^2$ in the above formula (1) with bromine, respectively, wherein the reaction is carried out in the presence of a solvent which is inactive in the reaction, and 80% or more of the theoretical amount of the heat gene rated by the reaction is removed from the reactor by the vaporization of the solvent.

2. The method of claim 1 for the production of a bromine compound, wherein 85% or more of the theoretical amount of the heat generated by the reaction is removed from the reactor by the vaporization of the solvent.

3. The method of claim 1 for the production of a bromine compound, wherein the solvent has a boiling point at normal pressure of 0 to 100° C.

4. The method of claim 1 for the production of a bromine compound, wherein the solvent is a halogenated hydrocarbon.

5. The method of claim 1 for the production of a bromine compound, wherein the solvent is used in an amount of 2 to 1000 mols based on 1 unsaturated group of the compound represented by the above formula (1).

6. The method of claim 1 for the production of a bromine compound, wherein 1 to 5 mol of bromine is used based on 1 unsaturated group of the compound represented by the above general formula (1).

7. The method of claim 1 for the production of a bromine compound, wherein the reaction is carried out at a temperature of 0 to 60° C.

8. The method of claim 1 for the production of a bromine compound, wherein an alcohol represented by the following formula (3) is added to the reaction system:

$$R^5—(OH)_n \quad (3)$$

wherein $R^5$ is an aliphatic group having 1 to 6 carbon atoms and valence of n, and n is an integer of 1 to 4.

9. The method of claim 1 for the production of a bromine compound, wherein the alcohol is used in an amount equivalent to 0.5 to 20 hydroxyl groups based on 100 unsaturated groups in the formula (1) compound feed to the reactor.

10. The method of claim 1 for the production of a bromine compound, wherein the reaction is carried out in the presence of 10 or less mol of water based on 100 unsaturated groups in the formula (1) compound feed to the reactor.

11. A continuous method for the production of a bromine compound comprising reacting in a reactor a compound having an aliphatic unsaturated bond represented by the above formula (1) with bromine to produce a bromine compound represented by the above formula (2), wherein the method comprises the steps of continuously supplying into the rector the compound represented by the formula (1), bromine and a solvent, which is inactive in the reaction, separately or as mixtures of combinations thereof in such a ratio that the number of mols of bromine based on 1 unsaturated group of the compound represented by the formula (1) is 1 to 5, and reacting them with each other while 80% or more of the theoretical amount of the heat of reaction is removed by the vaporization of the solvent in the reactor, taking out a reaction mixture from the reactor, and recovering the bromine compound represented by the above formula (2) from the reaction mixture.

12. The continuous method of claim 11 for production of a bromine compound, wherein the compound having an aliphatic unsaturated group and bromine are supplied continuously into the reactor through a flow mixer as a mixture solution together with at least part of the solvent as required.

13. The continuous method of claim 12 for the production of a bromine compound, wherein the flow rate of the solution in the flow mixer is 15 to 500 cm/sec.

14. The continuous method of claim 12 for the production of a bromine compound, wherein the residence time of the solution in the flow mixer is 0.01 to 180 sec.

15. The continuous method of claim 12 for the production of a bromine compound, wherein the flow mixer is a static mixer.

16. The continuous method of claim 12 for the production of a bromine compound, wherein the flow mixer is a static mixer having 4 to 20 elements.

17. A flame retardant composition comprising
(i) a bromine compound represented by the following formula (2) in an amount of 90% by weight or more, $$R^3-O-Ar^1-Y-Ar^2-O-R^4 \quad (2)$$

wherein $AR^1$ and $AR^2$ may be the same or different and are each an aromatic hydrocarbon group having 5 to 16 carbon atoms or saturated alicyclic hydrocarbon group having 5 to 12 carbon atoms, the $Ar^1$ and $Ar^2$ hydrocarbon groups can be substituted by at least one halogen; Y is a saturated hydrocarbon group having 1 to 6 carbon atoms, sulfone group, sulfide group, ketone group, alkylene oxide group having 2 to 6 carbon atoms or single bond; $R^3$ and $R^4$ may be the same or different and are each a hydrocarbon group having 2 to 11 carbon atoms to which a bromine atom is added, and
(ii) a hydroxy bromine compound represented by the following formula (4) in an amount of 0.0001 to 0.02 mol % based on 1 mol of the bromine compound,

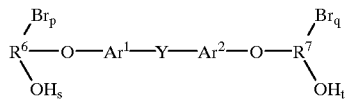
(4)

wherein $Ar^1$, $Ar^2$ and Y are the same as defined in the above formula (1), $R^6$ and $R^7$ may be the same or different and are each a hydrocarbon group having 2 to 11 carbon atoms, p and q are each an integer of 0 to 10, provided that p+q is an integer of 1 or more, and s and t are each an integer of 0 to 5, provided that s+t is an integer of 1 or more.

18. The flame retardant composition of claim 17 wherein in the formula (4) p+q is an integer of 2 to 10, and s+t is an integer of 1 to 5.

* * * * *

UNITED STATES PATENT AND TRADEMARK OFFICE
CERTIFICATE OF CORRECTION

PATENT NO.  : 5,998,674
DATED       : Dec. 7, 1999
INVENTOR(S) : Yutaka TAKETANI; Haruhisa HOSHIMI; Masanori MONRI; Seiichi TANABE; Yasuhiro SHIMIDZU It is certified that error appears in the above-indentified patent and that said Letters Patent is hereby corrected as shown below:

ON TITLE PAGE:

Between line 22 and line 51, insert

--Foreign Application Priority Data

| August 22, 1997    | [JP] | Japan | 226266   |
| August 28, 1997    | [JP] | Japan | 232430   |
| September 3, 1997  | [JP] | Japan | 238367   |
| December 3, 1997   | [JP] | Japan | 332940   |
| December 4, 1997   | [JP] | Japan | 334143   |
| December 5, 1997   | [JP] | Japan | 335787-- |

Signed and Sealed this

First Day of May, 2001

Attest:

NICHOLAS P. GODICI

Attesting Officer     Acting Director of the United States Patent and Trademark Office